US011055726B2

(12) United States Patent
Akgun et al.

(10) Patent No.: US 11,055,726 B2
(45) Date of Patent: Jul. 6, 2021

(54) INTEGRATED FUEL TRACKING METHOD OF AUTHENTICATION IN A FUEL DISTRIBUTION NETWORK

(71) Applicant: KUANTAG NANOTEKNOLOJILER GELISTIRME VE URETIM A.S., Istanbul (TR)

(72) Inventors: Osman Vedat Akgun, Izmir (TR); Emre Heves, Istanbul (TR)

(73) Assignee: Kuantag Nanoteknolojiler Gelistirme ve Uretim A.S., Istanbul (TR)

( * ) Notice: Subject to any disclaimer, the term of this patent is extended or adjusted under 35 U.S.C. 154(b) by 530 days.

(21) Appl. No.: 16/047,940

(22) Filed: Jul. 27, 2018

(65) Prior Publication Data

US 2018/0349919 A1    Dec. 6, 2018

Related U.S. Application Data

(63) Continuation of application No. 14/743,677, filed on Jun. 18, 2015, now abandoned.

(51) Int. Cl.
*G01N 33/20* (2019.01)
*G06Q 30/00* (2012.01)
(Continued)

(52) U.S. Cl.
CPC .......... *G06Q 30/018* (2013.01); *B67D 7/342* (2013.01); *G06F 16/2358* (2019.01);
(Continued)

(58) Field of Classification Search
CPC ...................................................... G01N 33/22
(Continued)

(56) References Cited

U.S. PATENT DOCUMENTS 3,704,952 A * 12/1972 Bird ........................ G01N 21/72
356/315
3,861,886 A * 1/1975 Meloy ........................ G09F 3/00
436/56
(Continued)

FOREIGN PATENT DOCUMENTS

AU      2012100395 A4    5/2012
EP      0257559 A2    3/1988
(Continued)

OTHER PUBLICATIONS

Hu, S.; Gao, X., Stable Encapsulation of Quantum Dot Barcodes with Silica Shells, Adv. Funct. Mater., 2010, 20, 3721-3726.
(Continued)

*Primary Examiner* — Arlen Soderquist
(74) *Attorney, Agent, or Firm* — Halit N. Yakupoglu

(57) ABSTRACT

A system for tracking fuel in a fuel distribution network is provided. The system includes a plurality of tracking devices disposed at a plurality of fuel transport locations including a supplier fuel storage location, a mobile fuel storage location, a stationary fuel storage location and a vehicle fuel location, wherein each tracking device is configured to read in real time the digital tag by receiving a radiation emission spectrum associated with the fuel identification information as the fuel is transported through the plurality of fuel transfer locations. The digital tag includes information about the fuel.

20 Claims, 9 Drawing Sheets

(51) Int. Cl.
| | |
|---|---|
| *G06F 16/23* | (2019.01) |
| *G06F 16/2458* | (2019.01) |
| *G06F 16/2457* | (2019.01) |
| *H04W 4/029* | (2018.01) |
| *H04W 4/40* | (2018.01) |
| *B67D 7/34* | (2010.01) |
| *G07C 3/00* | (2006.01) |
| *G07C 3/14* | (2006.01) |
| *G06K 7/10* | (2006.01) |
| *G06K 7/12* | (2006.01) |
| *H04W 4/44* | (2018.01) |
| *G01N 33/28* | (2006.01) |
| *B67D 7/32* | (2010.01) |

(52) U.S. Cl.
CPC .... *G06F 16/2477* (2019.01); *G06F 16/24573* (2019.01); *G06F 16/24575* (2019.01); *G06K 7/10435* (2013.01); *G06K 7/10841* (2013.01); *G06K 7/12* (2013.01); *G07C 3/00* (2013.01); *G07C 3/143* (2013.01); *H04W 4/029* (2018.02); *H04W 4/40* (2018.02); *H04W 4/44* (2018.02); *B67D 7/3281* (2013.01); *G01N 33/2882* (2013.01)

(58) Field of Classification Search
USPC ............. 422/82.05–82.09, 82.11; 436/27, 56
See application file for complete search history.

(56) References Cited

U.S. PATENT DOCUMENTS

| | | | |
|---|---|---|---|
| 4,247,899 A * | 1/1981 | Schiller | B67D 7/04 |
| | | | 705/413 |
| 4,250,550 A * | 2/1981 | Fleischer | B67D 7/14 |
| | | | 705/413 |
| 4,649,711 A | 3/1987 | Sibley et al. | |
| 4,745,285 A | 5/1988 | Recktenwald et al. | |
| 5,229,298 A | 7/1993 | Zoumalan | |
| 5,279,967 A | 1/1994 | Bode | |
| 5,358,873 A | 10/1994 | Nowak | |
| 5,359,522 A | 10/1994 | Ryan | |
| 5,420,797 A | 5/1995 | Burns | |
| 5,525,516 A | 6/1996 | Krutak et al. | |
| 5,652,810 A | 7/1997 | Tipton et al. | |
| 5,710,046 A | 1/1998 | Rutledge et al. | |
| 5,722,469 A * | 3/1998 | Tuminaro | B67D 7/342 |
| | | | 141/83 |
| 5,723,338 A | 3/1998 | Rutledge et al. | |
| 5,742,064 A | 4/1998 | Infante | |
| 5,878,178 A | 3/1999 | Wach | |
| 5,878,772 A | 3/1999 | Belyea | |
| 5,928,954 A | 7/1999 | Rutledge et al. | |
| 5,958,780 A | 9/1999 | Asher et al. | |
| RE36,510 E * | 1/2000 | Burns | B67D 7/145 |
| | | | 221/23 |
| 6,274,381 B1 | 8/2001 | Pauls et al. | |
| 6,312,958 B1 | 11/2001 | Meyer et al. | |
| 6,576,155 B1 | 6/2003 | Barbera-Guillem | |
| 6,598,792 B1 | 7/2003 | Michot et al. | |
| 6,691,557 B1 | 2/2004 | Rice | |
| 6,692,031 B2 | 2/2004 | McGrew | |
| 6,881,381 B1 | 4/2005 | Asher et al. | |
| 7,466,400 B2 | 12/2008 | Luther et al. | |
| 7,763,469 B2 | 7/2010 | Babichenko et al. | |
| 8,158,432 B2 | 4/2012 | Grof et al. | |
| 8,384,891 B2 | 2/2013 | Carr et al. | |
| 8,574,323 B2 | 11/2013 | Green et al. | |
| 8,592,213 B2 | 11/2013 | Wilkinson et al. | |
| 8,744,723 B2 | 6/2014 | Jones | |
| 8,805,592 B1 | 8/2014 | Booth et al. | |
| 9,791,407 B2 | 10/2017 | Urey et al. | |
| 9,810,632 B2 | 11/2017 | Urey et al. | |
| 2002/0164271 A1 | 11/2002 | Ho | |
| 2004/0248307 A1 | 12/2004 | Grof et al. | |
| 2004/0262400 A1 | 12/2004 | Chang et al. | |
| 2005/0066576 A1 * | 3/2005 | Morris | G01F 9/00 |
| | | | 44/639 |
| 2005/0165554 A1 | 7/2005 | Betancourt et al. | |
| 2005/0241989 A1 | 11/2005 | Sant et al. | |
| 2005/0260764 A1 | 11/2005 | Grigsby et al. | |
| 2006/0118741 A1 | 6/2006 | Ross et al. | |
| 2006/0173362 A1 | 8/2006 | Toms et al. | |
| 2006/0190129 A1 * | 8/2006 | DeLine | B67D 7/04 |
| | | | 700/232 |
| 2007/0064323 A1 | 3/2007 | Luther et al. | |
| 2007/0088600 A1 | 4/2007 | Lichtinger et al. | |
| 2007/0178596 A1 | 8/2007 | Babichenko et al. | |
| 2008/0002927 A1 | 1/2008 | Furnish | |
| 2008/0021983 A1 | 1/2008 | Dodson | |
| 2008/0215719 A1 | 9/2008 | Swan | |
| 2009/0289113 A1 | 11/2009 | Vilnai et al. | |
| 2009/0299805 A1 * | 12/2009 | Baughman | G06Q 10/08 |
| | | | 705/70 |
| 2009/0307032 A1 | 12/2009 | Tribe et al. | |
| 2009/0315729 A1 * | 12/2009 | Inhoffer | B64F 1/28 |
| | | | 340/632 |
| 2009/0322544 A1 | 12/2009 | McDowell | |
| 2010/0089486 A1 | 4/2010 | Koeninger et al. | |
| 2010/0208243 A1 | 8/2010 | Suzuki et al. | |
| 2010/0222917 A1 | 9/2010 | Bohlig et al. | |
| 2010/0305885 A1 | 12/2010 | Ganapathy et al. | |
| 2011/0040503 A1 | 2/2011 | Rogers et al. | |
| 2011/0101094 A1 | 5/2011 | Call | |
| 2011/0120589 A1 | 5/2011 | Evans | |
| 2011/0130882 A1 | 6/2011 | Perez | |
| 2011/0177494 A1 | 7/2011 | Ismagilov et al. | |
| 2011/0229983 A1 | 9/2011 | Wilkinson et al. | |
| 2012/0034702 A1 | 2/2012 | Croud et al. | |
| 2012/0035442 A1 | 2/2012 | Barman et al. | |
| 2012/0054201 A1 | 3/2012 | Fischer | |
| 2012/0104278 A1 | 5/2012 | Downing et al. | |
| 2012/0205449 A1 | 8/2012 | Lewis et al. | |
| 2012/0301872 A1 | 11/2012 | Tormod | |
| 2013/0009119 A1 | 1/2013 | Natan et al. | |
| 2013/0035422 A1 * | 2/2013 | Freund | C04B 40/0096 |
| | | | 524/2 |
| 2013/0155402 A1 | 6/2013 | Walton et al. | |
| 2013/0179090 A1 | 7/2013 | Conroy et al. | |
| 2013/0283893 A1 | 10/2013 | Earl et al. | |
| 2014/0129038 A1 * | 5/2014 | Finnell | B67D 7/344 |
| | | | 700/283 |
| 2014/0170754 A1 | 6/2014 | Liu et al. | |
| 2014/0236444 A1 | 8/2014 | Stefan et al. | |
| 2015/0300983 A1 | 10/2015 | Urey et al. | |
| 2016/0371704 A1 * | 12/2016 | Akgun | G06F 16/2477 |

FOREIGN PATENT DOCUMENTS

| | | | |
|---|---|---|---|
| EP | 0358203 A1 | | 3/1990 |
| EP | 0489347 A1 | | 6/1992 |
| EP | 513604 | * | 11/1992 |
| EP | 0935750 B1 | | 4/2002 |
| EP | 1441227 A2 | | 7/2004 |
| EP | 1794764 B1 | | 7/2011 |
| GB | 1596521 A | | 8/1981 |
| GB | 2437276 | * | 10/2007 |
| JP | 2010-254346 | * | 11/2010 |
| WO | 9412874 A1 | | 6/1994 |
| WO | 99/52708 | * | 10/1999 |
| WO | 0177391 A1 | | 10/2001 |
| WO | 02098199 A2 | | 12/2002 |
| WO | 2005/052560 | * | 6/2005 |
| WO | 2006036388 A2 | | 4/2006 |
| WO | 2008/017180 | * | 2/2008 |
| WO | 2008019448 A1 | | 2/2008 |
| WO | 2009026665 A1 | | 3/2009 |
| WO | 2009063471 A2 | | 5/2009 |
| WO | 2009120563 A1 | | 10/2009 |
| WO | 2010089587 A2 | | 8/2010 |
| WO | 2011037894 A1 | | 3/2011 |
| WO | 2011123938 A1 | | 10/2011 |

(56) References Cited

FOREIGN PATENT DOCUMENTS

| WO | 2011132079 A1 | 10/2011 |
| WO | 2013079974 A1 | 6/2013 |
| WO | 2013126028 A2 | 8/2013 |
| WO | 2014063725 A1 | 5/2014 |
| WO | 2014087359 A1 | 6/2014 |
| WO | 2016010494 A1 | 1/2016 |
| WO | 2016203306 A1 | 12/2016 |

OTHER PUBLICATIONS

PCT, International Search Report and Written Opinion; Patent Application No. PCT/IB2016/000835 (dated Sep. 2, 2016).

* cited by examiner

INTEGRATED FUEL TRACKING METHOD OF AUTHENTICATION IN A FUEL DISTRIBUTION NETWORK

FIELD

The present invention generally relates to fuel identification and tracking, more particularly, to a method, apparatus and system for identification and tracking of fuels in real time.

BACKGROUND

Today oil is the fuel of choice for most of the transportation modes in the world. In fact, more than 50 percent of oil used around the world is consumed by the transportation sector. In particular, approximately 75 percent of the oil consumed by overall transportation sector is in the field of road transportation. This is because oil is currently the only fuel which has a distinctive combination of availability, portability, affordability and high energy density factors.

In many developed and developing countries, oil and gas industries are very important because excise tax revenues from fuel sales contribute their economies. Especially in growing economies, high excise tax can add up to the price of fuel.

Due to its monetary value and the transportation sector's dependence on fuel, fuel smuggling, fuel adulteration and fuel tax evasions have become a growing problem in some countries and pose serious threats to the revenues of such countries as well as energy companies worldwide. The most common way of adulteration involves blending or diluting high quality branded fuel products with inferior products, such as diluting gasoline with cheaper kerosene. Since the key chemistry of the branded fuel is still present in such blended fuel, an expensive and time consuming quantitative analysis is often required to detect such dilution with an inferior product. Estimated economic value of such improper actions is in the range of billions of USD per year. Therefore, fuel supply integrity and quality are of vital importance for fuel tax revenues.

Some conventional techniques for detecting fuel adulteration in a fuel product often require collecting fuel samples for testing in laboratories away from fuel storage or transfer locations, which can be time consuming and expensive. Some other conventional techniques rely on on-field or off-field bulky analysis equipment such as spectrometers to test the fuel product to detect adulteration, which techniques are also time consuming and expensive as well as require trained operators.

Thus, it will become readily apparent that it would be highly desirable to provide systems and methods which can monitor fuel distribution networks effectively to protect the integrity and the quality and the fuel supply as well as to enable secure fuel tax collection and prevent revenue losses.

SUMMARY

The present inventions are related to fuel identification and tracking, more particularly, to a method, apparatus and system for a real time identification and tracking of fuels. An aspect of the present invention includes a system for tracking fuel in a fuel distribution network, including: a plurality of tracking devices for tracking a fuel including a digital tag carrying a fuel identification information, the plurality of tracking devices being disposed in a plurality of fuel transfer locations including a supplier fuel storage location, a mobile fuel storage location, a stationary fuel storage location and a vehicle fuel location, wherein each tracking device is configured to read in real time the digital tag by receiving a radiation emission spectrum associated with the fuel identification information as the fuel is transported through the plurality of fuel transfer locations; and a system server in communication with the plurality of tracking devices to receive the fuel identification information carried by the digital tag, the system server being configured to determine whether the fuel identification information received from the plurality of tracking devices is valid and the same, wherein the system server includes a data base and a system communication module which is configured to communicate with the data base and a plurality of external data bases.

Another aspect of the present invention includes a method of real time tracking of fuel, including: identifying a fuel contained in a first fuel transfer location by adding a digital tag material; real time reading a first digital tag information from the digital tag material by a first sensor module during a first fuel transfer operation as the fuel is unloaded from the first fuel location for a second fuel transfer location; real time reading a second digital tag information from the digital tag material by a second sensor module during the first fuel transfer operation as the fuel from the first fuel location is loaded into the second transfer location; transmitting the first digital tag information and the second digital tag information to a server having a database; determining whether the second digital tag information is the same as the first digital tag information; generating a tracking data about the first fuel transfer operation; and storing the tracking data about the first fuel transfer operation in the database.

Yet another aspect of the present invention includes a sensor module for tracking fuel, including: a controller; a communication module connected to the controller; at least one sensor connected to the controller and is configured to in-situ detect a digital tag within the fuel and in real time manner as the fuel is flowed through one location to another, wherein the at least one sensor comprising: at least one light detector; at least one light source; a first light guide configured to emit light in a predetermined spectral range to fluoresce the digital tag within the fuel, wherein the first light guide is a distal end of an optical fiber transmitting light from the light source; and a second light guide configured to receive fluorescence emitted by the digital tag, wherein the second light guide is a distal end of an optical fiber connected to the light detector, and the first light guide and the second light guide are bundled together and are in direct contact with the fuel being tracked.

BRIEF DESCRIPTION OF THE DRAWINGS

These and other aspects and features of the present invention will become apparent to those of ordinary skill in the art upon review of the following description of specific embodiments of the invention in conjunction with the accompanying figures, wherein.

DETAILED DESCRIPTION

Figure 1:
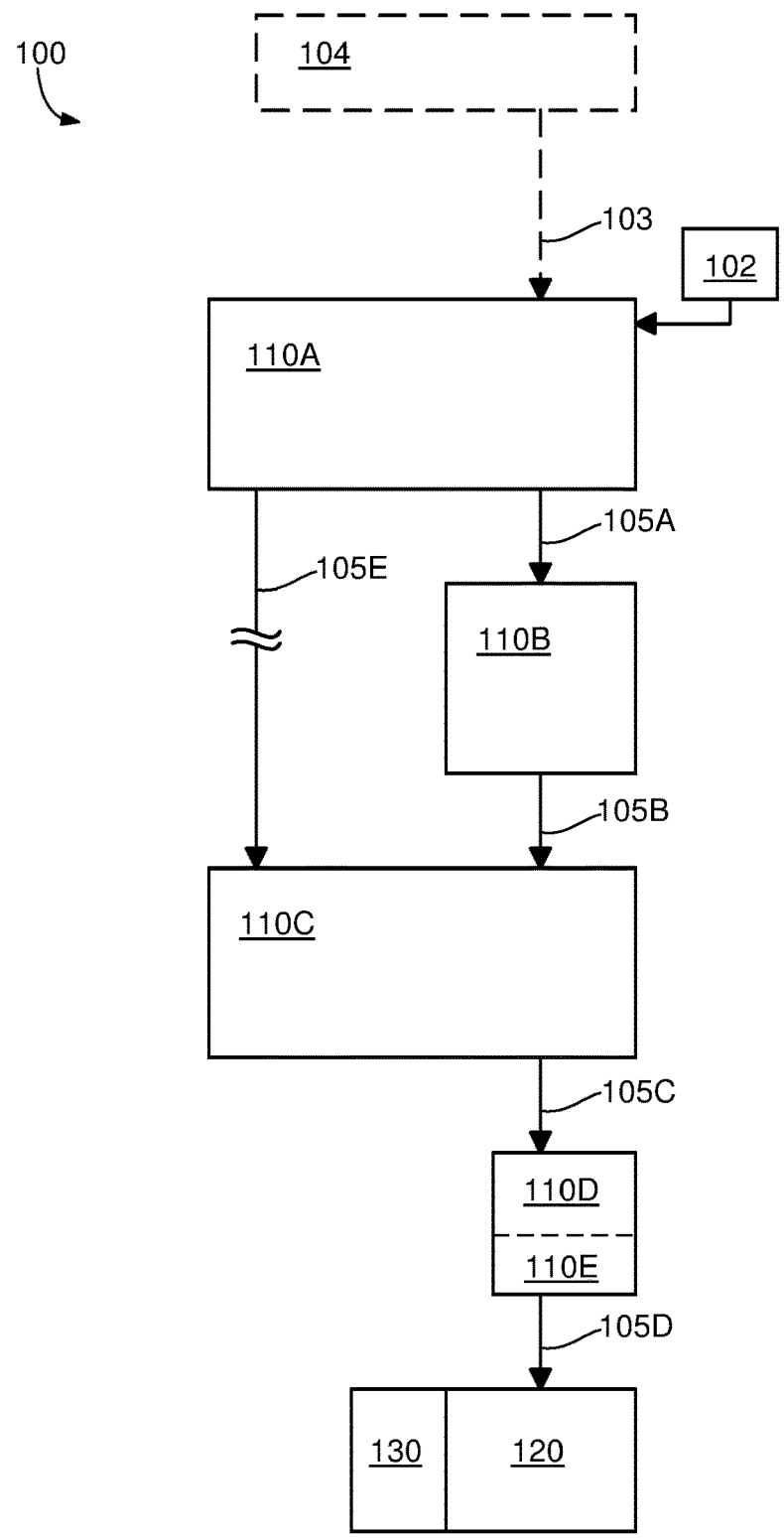
FIG. 1 is a schematic block diagram of an exemplary fuel distribution network of the present invention.

The present invention relates to a system for marking, tracking, monitoring of liquids in order to detect unwanted alteration of liquids during transportation, storage or usage, and its methods thereof. In some embodiments, the liquid may be a fuel such as gasoline or diesel, oil or the like, and/or any combination thereof. Embodiments of the present invention provide systems and methods for tagging, tracking, monitoring of fuels or altered fuels in order to detect unwanted or illegal alterations of fuels during transportation, storage or usage. For the purposes of the present invention, the term "altered fuel" is understood to mean a fuel that has been mixed, diluted, and/or adulterated. A fuel can be altered by being mixed, diluted, and/or adulterated with one or more other fuels, solvents, oils, petrochemicals and/or any combination thereof. The term 'fuel' used herein is understood to mean any hydrocarbons, petroleum based products, biofuels, fossil fuels including, but not limited to, gasoline, diesel, kerosene, and engine oils.

In some embodiments, the present invention may provide integrated systems and methods for identifying and tracking fuel in fuel supply chains, or fuel distribution networks, which fuel supply chains may for example include: fuel refineries; one or more fuel delivery, handling shipping or transportation systems, such as fuel tanks, pipelines or fuel trucks; and end-users or consumer vehicles such as automobiles powered by that particular fuel.

In one embodiment, a system of the present invention may include a plurality of fuel tracking locations or fuel tracking points, which may generally be located at fuel transfer or transport locations including fuel storage facilities or containers, including at least one fuel supplier storage location, e.g., a refinery terminal, at least one mobile fuel storage location, e.g. a tanker truck, at least one stationary fuel storage location, e.g., a gas station with gas pump, and at least one fuel consumer or vehicle fuel location, e.g., a fuel consumer vehicle. In one embodiment, the fuel may be tracked and identified by identifying and tracking a digital tag in the fuel at fuel tracking locations as this digitally tagged fuel is distributed through a fuel distribution network. It is understood that for the purposes of this application, "digitally tagged fuel" refers to a fuel mixed with at least one digital tag.

In one embodiment, the tracking locations include a plurality of sensor modules including sensor units or other units configured to detect and read the digital tag in the fuel. Sensor modules may be used to track and identify a digitally tagged fuel in real-time throughout the fuel distribution network by initiating a tracking operation from refineries, through various storage or transportation terminals to fuel users, consumers or clients using the digitally tagged fuel for their vehicles. Sensor modules may be configured to in-situ detect or read a code or coded information carried by a digital tag within the fuel in real time as the fuel is transported through the fuel distribution network. A digital tag may carry a including information identifying a selected fuel. In one embodiment, a digital tag may include any desired information proving fuel's integrity, such as fuel type, fuel company identification, brand name identification, information about fuel's approved quality and an indication that the fuel is taxed, and the like. Digital tag may also include other information such as refinery identification, production lot of the fuel, a product ID, or a number or code for the fuel to identify it.

Turning now to the Figures, FIG. 1 shows an exemplary fuel distribution network 100 or fuel distribution chain distributing a digitally tagged fuel. As will be explained below, in one embodiment, a digitally tagged fuel distributed within the network 100 may be tracked and identified in real time using a tracking and identification system of the present invention depicted in FIG. 2.

The fuel distribution network 100 may include a plurality of fuel transfer locations 110 and a plurality of fuel consumer locations 120. A first fuel transfer location 110A of the network 100 may be a fuel supplier location, a fuel terminal or oil refinery where the fuel being initially stored and digitally tagged, i.e., a digital tag is added to the fuel, and where the digitally tagged fuel distribution may be initiated. The first fuel transfer location 110A may include one or more fuel storage containers to contain the digitally tagged fuel which is formed by adding a digital tag including a digital tag material from a digital tag supply unit 102 into refinery fuel or branded fuel that will be tracked. Optionally, the first fuel transfer location 110A may be a fuel terminal adjacent a refinery (not shown) or a location outside a refinery so that a refinery fuel flow 103 including the refinery fuel may be optionally transported via a refinery supply truck 104 and delivered to the first fuel transfer location 110A. The digital tag may be added to the refinery fuel in very small amounts, preferably, within less than ppm (parts per million) range, or within the range of ppb (parts per billion). The digital tag may include one or more codes related to information about the fuel type such as whether it is gasoline or diesel; the octane rating of the fuel; and the may be company specific, i.e., identifying the oil company, fuel brand name with the fuel type. Such information about the digitally tagged fuel corresponding to the assigned identification code is stored in the system data storage to be used.

A second fuel transfer location 110B of the fuel distribution network 100, which may be a fuel transport vehicle, such as a tanker truck, ship, airplane or train to transport fuel, receives a first tagged fuel flow 105A including the digitally tagged fuel, from the first fuel transfer location 110A. A third fuel transfer location 110C of the fuel distribution network 100 receives a second tagged fuel flow 105B including the digitally tagged fuel from the second fuel transfer location 110B. The third fuel transfer location 110C may be a fuel storage tank at a fuel sales location such as a fuel storage tank of a gas station. A third tagged fuel flow 105C including the digitally tagged fuel from the third fuel transfer location 110C may be received by a fourth fuel transfer location 110D of the fuel distribution network 100, such as a fuel pump, preferably integrated with a fifth fuel transfer location 110E, such as a fuel pump gun or nozzle dispenser to dispense fuel.

Finally, a fuel consumer location 120 of the fuel distribution network 100, such as a gas tank of a consumer vehicle (not shown) with an engine 130 to use the digitally tagged fuel to operate the consumer vehicle. The consumer vehicle may be a car, truck or any vehicle having an engine using fuel to operate. The fuel consumer location 120 receives a fourth tagged fuel flow 105D including the digitally tagged fuel from the fifth fuel transfer location 110E. Optionally, a fifth tagged fuel flow 105E including the digitally tagged fuel may be directly delivered to the third fuel transfer location 110C from the first fuel transfer location 110A using for example a pipeline (not shown) connecting the first fuel transfer location 110A to the third fuel transfer location 110C. Although it may preferably be added to the refinery fuel contained in the first fuel transfer location 110A, the digital tag may be directly injected into the refinery fuel flow filling the first transfer location 110A. In other embodiments, the refinery fuel may be initially filled into the first fuel transfer location 110A without adding the digital tag, and then the digital tag may be injected into a refinery fuel flow from the first fuel transfer location 110A as it is delivered to other transfer locations from the first fuel transfer location.

Figure 2:
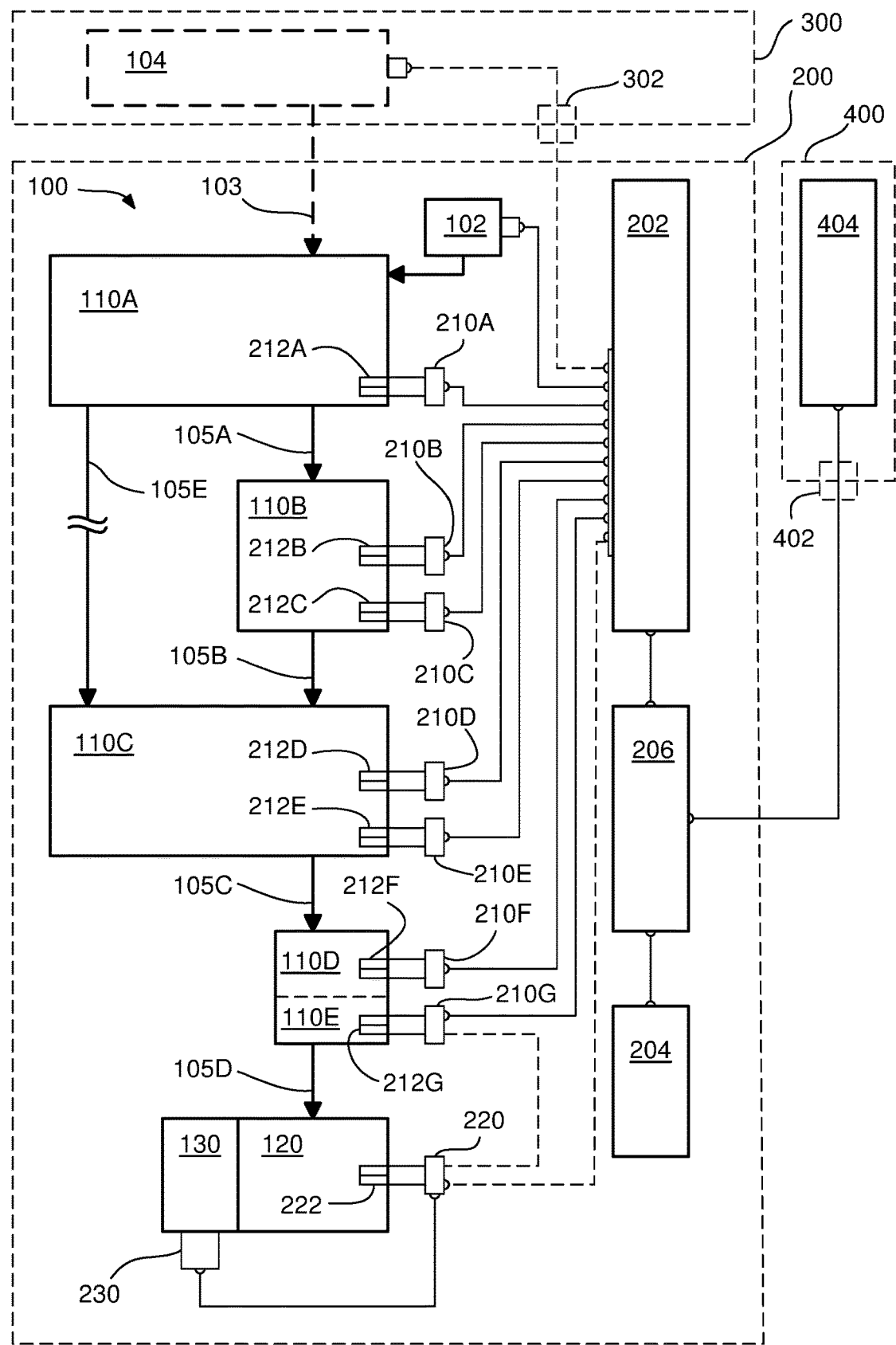
FIG. 2 is a schematic diagram of an embodiment of a fuel tracking an identification system of the exemplary fuel distribution network shown in FIG. 1.

FIG. 2 shows an embodiment of a tracking and identifying integrated system 200 for the exemplary fuel distribution network 100 to real time track and identify the digitally tagged fuel within the network 100 described above. Accordingly, the above described exemplary fuel transfer locations, namely, the first fuel transfer location 110A, the second fuel transfer location 110B, the third fuel transfer location 110C, the fourth fuel transfer location 110D, the fifth fuel transfer location 110E and the fuel consumer location 120 may include tracking locations or tracking points that the digitally tagged fuel may be tracked and identified by the system 200. The system 200 includes a system server 202 which may be in communication with a system data storage module 204 or a data base through a system communication module 206. The system 200 may also include a system memory module (not shown).

The system server 202 may typically include a processing unit or processor, a memory unit, various communication interfaces, an operation software or other software, computer program products, a monitor with many display options, data retrieval and data entry tools such as a keyboard, mouse and/or touch screen display pointing devices. System server 202 may be the heart of the system 200, which may receive and register encrypted digital tag information sent by the service sensor modules (SSMs), client sensor modules (CSMs) and other type of information sent by other modules which may be installed throughout the fuel distribution network 100 to track other qualitative and quantitative information such as transfer locations, transferred fuel quantities, vehicle identity, and the like. With the fuel tracking and identifying system 200 of the present invention, the transport of the digitally tagged fuel throughout the fuel distribution network 100 may be tracked and identified in real time using SSMs and CSMs disposed at fuel tracking points at each fuel transfer location of the exemplary fuel distribution network 100. The system database 204 of the system 200 may store very large data including, but not limited to, all the reports, documents, information with regard to the fuel distribution and the vehicles computer instructions to perform tasks. This data can be accessed by the system server 202 through the system communication module 206. The system data storage module 204 may include a data library of previously decided digital tag information or ID or code identifying each digitally tagged fuel distributed within the network 100, i.e., information carried by the digital tag, in a first data library. Digital tag information or code identifies the digitally tagged fuel by brand name, company, fuel type, country, a trademark, quality indicators, and the like, which are previously mentioned. In a second data library, the system data storage module 204 may further include the digital tag information read or detected by the SSMs as the digitally tagged fuel is tracked as it is distributed.

In one embodiment, as the digitally tagged fuel is being transported within the network 100, the system server 202 compares in real time the digital tag reading from the SSMs and CSMs, which are stored in the second data library, with the digital tag data of the same fuel stored in the first data library to track and authenticate the digitally tagged fuel. The data kept in the system data storage module 204 may further include vehicle ID data identifying the vehicles receiving the digitally tagged fuel, GPS location data identifying location of each fuel transfer, timestamp data identifying time of the fuel transfer, and the transferred fuel quantity data from the fuel transfer locations. In addition to the system data storage, each SSM and each CSM may also store the same data at their data storages. The system data storage module 204 and the system memory module (not shown) may be in the form of non-transitory computer readable medium configured to store files and executable computer instructions. A computer program product stored on a non-transitory computer readable medium may include instructions executable by the processing unit or processor of the server to operate the system 200.

The system server 202 may also communicate with various external systems such as an external system 300 which may be an optional refinery system including servers (not shown) and databases (not shown) and employing the refinery supply truck 104 to deliver the refinery fuel to the first fuel transfer location 110A. The system server 202 of the system 200 may receive data about the refinery fuel from the refinery supply truck 104 via an external system communication module 302 of the external system 300.

Another external system 400 may include a server (not shown) and a data storage 404 containing vehicle and driver information. The system server 202 of the system 200 may be in data communication with the database 404 of the external system 400 through the system communication module 206 and the external system communication module 402 of the external system 400. The system 400 may be a system containing vehicle and driver related public information such as Department of Motor Vehicles (DMV) system (in the USA) or a traffic police headquarter system or other similar public or non-public record systems containing such vehicle and driver data, so as to check the vehicle and driver records to identify the driver and the vehicle or to confirm driver and vehicle identity. Such information about the vehicle may also be used for example (1) to generate system warnings about the identified vehicle or (2) optionally, in extreme cases, to prevent the vehicle from refueling by interrupting fuel flow to the vehicle using the SSM at the fuel pump if the information detected by the CSM generates error signals because of a suspicious previous activity, for example: a previous refueling activity done at an unknown location, or an unknown service station or facility.

In one embodiment, the system server 202 may include service sensor modules 210 such as a first SSM 210A, a second SSM 210B, a third SSM 210C, a fourth SSM 210D, a fifth SSM 210E, a sixth SSM 210F and a seventh SSM 210G as well as one or more client sensor modules CSM 220 to track and identify digitally tagged fuel distributed in the network 100. The system server 202 registers data from each sensor module with sensor module identification (sensor ID) including sensor's location.

Referring back to FIG. 2, the first service sensor module (SSM) 210A including a sensor probe 212A may be located at the first fuel transfer location 110A or the first fuel tracking location, preferably adjacent a fuel outlet of the first fuel transfer location 110A. The sensor probe 212A may be in contact with the digitally tagged fuel in the first fuel transfer location 110A to read the digital tag in real time and in-situ within the digitally tagged fuel. As explained above, the first fuel transfer location 110A may be a fuel supplier location, an oil refinery fuel storage tank or terminal storage location having fuel storage facilities where the fuel is initially stored and digitally tagged using the digital tag material delivered from the digital tag supply unit 102, and where the digitally tagged fuel begins its distribution cycle within the fuel distribution network 100.

The first SSM 210A may include a location identification (ID) information indicating that it is located at the fuel outlet of the first fuel transfer location 110A, e.g., the refinery or terminal storage tank. The first SSM 210A may gather the following data from the fuel outlet of the first fuel transfer location 110A: (a) the digital tag information in the first tagged fuel flow 105A when it is transferred from the first transfer location 110A to the second transfer location 110B; (b) transferred fuel quantity gathered from the fuel gauges on the first transfer location 110A and/or the second transfer location 110B; (c) GPS data indicating the location or geographical location of the first SSM 210A. The first SSM 210A may communicate with the system server 202 to provide or upload the following data from the first fuel transfer location 110A: the location ID information; digital tag information; transferred fuel quantity, a time stamp for the fuel transfer operation; GPS information and location information. The digital tag supply unit 102 may also be in data communication with the system server 202 to report about the digital tag material such as type and quantity of digital tag material used, and the like information.

The second SSM 210B including a sensor probe 212B may be located adjacent a fuel inlet of the second fuel transfer location 110B or the second fuel tracking location, which may be a fuel tanker truck for transporting fuel. The sensor probe 212B may be in contact with the first tagged fuel flow 105A flowing into the second fuel transfer location 110B to read the digital tag in real time and in-situ within the digitally tagged fuel. The second SSM 210B may include a location identification (ID) information indicating that it is located at the fuel inlet of the second fuel transfer location 110B, e.g., the fuel tanker truck. The second SSM 210B may gather the following data from the fuel inlet of the second fuel transfer location 110B: (a) the digital tag information in the first tagged fuel flow 105A when it is transferred from the first fuel transfer location 110A to the second fuel transfer location 110B; (b) transferred fuel quantity information gathered from the fuel gauges on the first fuel transfer location 110A and/or the second transfer location 110B; (c) GPS data indicating the location or geographical location of the SSM 210B. The second SSM 210B may communicate with the system server 202 to provide or upload the following data from the fuel inlet of the second fuel transfer location 110B: the location ID information; digital tag information; transferred fuel quantity, a time stamp for the fuel transfer operation; GPS information and location information.

The third SSM 210C including a sensor probe 212C may be located adjacent a fuel outlet of the second fuel transfer location 110B or the second fuel tracking location. The sensor probe 212C may be in contact with the second tagged fuel flow 105B flowing out of the second fuel transfer location 110B to read the digital tag in real time and in-situ within the digitally tagged fuel. The third SSM 210C may include a location identification (ID) information indicating that it is located at the fuel outlet of the second fuel transfer location 110B. The third SSM 210C may gather the following data from the fuel outlet of the second fuel transfer location 110B: (a) the digital tag information in the second tagged fuel flow 105B when it is transferred from the second transfer location 110B to the third transfer location 110C; (b) transferred fuel quantity information gathered from the fuel gauges on the second fuel transfer location 110B and/or the second fuel transfer location 110C; (c) GPS data indicating the location or geographical location of the SSM 210C. The third SSM 210C may communicate with the system server 202 to provide or upload the following data from the fuel outlet of the second fuel transfer location 110B: the location ID information; digital tag information; transferred fuel quantity, a time stamp for the fuel transfer operation; GPS information and location information.

The fourth SSM 210D including a sensor probe 212D may be located adjacent a fuel inlet of the third fuel transfer location 110C or the third fuel tracking location, which may be a gas station fuel storage tank for storing fuel for fuel pumps. The sensor probe 212D may be in contact with the second tagged fuel flow 105B flowing into the third fuel transfer location 110C to read the digital tag in real time and in-situ within the digitally tagged fuel. The fourth SSM 210D may include a location identification (ID) information indicating that it is located at the fuel inlet of the third fuel transfer location 110C, e.g., the fuel tanker truck. The fourth SSM 210D may gather the following data from the fuel inlet of the third fuel transfer location 110C: (a) the digital tag information in the second tagged fuel flow 105B when it is transferred from the second transfer location 110B to the third transfer location 110C; (b) transferred fuel quantity information gathered from the fuel gauges on the second fuel transfer location 110B and/or the third fuel transfer location 110C; (c) GPS data indicating the location or geographical location of the fourth SSM 210D. The fourth SSM 210D may communicate with the system server 202 to provide or upload the following data from the fuel inlet of the third fuel transfer location 110C: the location ID information; digital tag information; transferred fuel quantity, a time stamp for the fuel transfer operation; GPS information and location information.

The fifth SSM 210E including a sensor probe 212E may be located adjacent a fuel outlet of the third fuel transfer location 110C or the third fuel tracking location. The sensor probe 212E may be in contact with the third tagged fuel flow 105C flowing out of the third fuel transfer location 110C to read the digital tag in real time and in-situ within the digitally tagged fuel. The fifth SSM 210E may include a location identification (ID) information indicating that it is located at the fuel outlet of the third fuel transfer location 110C. The fifth SSM 210E may gather the following data from the fuel outlet of the third fuel transfer location 110C: (a) the digital tag information in the third tagged fuel flow 105C when it is transferred from the third fuel transfer location 110C to the fourth fuel transfer location 110D; (b) transferred fuel quantity information gathered from the fuel gauges on the third fuel transfer location 110C and/or the fourth fuel transfer location 110D; (c) GPS data indicating the location or geographical location of the fifth SSM 210E. The fifth SSM 210E may communicate with the system server 202 to provide or upload the following data from the fuel outlet of the third fuel transfer location 110C: the location ID information; digital tag information; transferred fuel quantity, a time stamp for the fuel transfer operation; GPS information and location information.

The sixth SSM 210F including a sensor probe 212F may be located adjacent a fuel inlet of the fourth fuel transfer location 110D or the forth fuel tracking location, which may be a gas station fuel pump which receives fuel from the gas station fuel storage when activated by a user and passes the fuel to the fuel gun or nozzle. The sensor probe 212F may be in contact with the third tagged fuel flow 105C flowing into the fourth fuel transfer location 110D to read the digital tag in real time and in-situ within the digitally tagged fuel. The sixth SSM 210F may include a location identification (ID) information indicating that it is located at the fuel inlet of the fourth fuel transfer location 110D, e.g., the fuel pump. The sixth SSM 210F may gather the following data from the fuel inlet of the fourth fuel transfer location 110D: (a) the digital tag information in the third tagged fuel flow 105C when it is transferred from the third fuel transfer location 110C to the fourth fuel transfer location 110D; (b) transferred fuel quantity information gathered from the fuel gauges on the third fuel transfer location 110C and/or the fourth fuel transfer location 110D; (c) GPS data indicating the location or geographical location of the sixth SSM 210F. The sixth SSM 210F may communicate with the system server 202 to provide or upload the following data from the fuel inlet of the fourth fuel transfer location 110D: the location ID information; digital tag information; transferred fuel quantity, a time stamp for the fuel transfer operation; GPS information and location information.

The seventh SSM 210G including a sensor probe 212G may be located adjacent a fuel outlet of the fifth fuel transfer location 110E or the fifth fuel tracking location, which may be a fuel nozzle, or fuel dispenser or fuel gun attachment of the gas station fuel pump. The fourth and fifth transfer locations 110D and 110E may be integrated locations, such as conventional fuel pump and a fuel gun which is attached to the fuel pump to discharge the fuel pumped by the fuel pump. The sensor probe 212G may be in contact with the fourth tagged fuel flow 105D flowing out of the sixth fuel transfer location 110E to read the digital tag in real time and in-situ within the digitally tagged fuel. The seventh SSM 210G may include a location identification (ID) information indicating that it is located at the fuel outlet of the fifth fuel transfer location 110E.

The seventh SSM 210G may gather the following data from the fuel outlet of the fifth fuel transfer location 110E: (a) the digital tag information in the fourth tagged fuel flow 105D when it is transferred from the fifth fuel transfer location 110E to the fuel consumer location 120, which may be a consumer vehicle to refuel at the gas station; (b) transferred fuel quantity information gathered from the fuel gauges on the fourth and fifth fuel transfer locations 110D and 110E and/or on the fuel consumer location 120; (c) GPS data indicating the location or geographical location of the seventh SSM 210G. The seventh SSM 210G communicates with the system server 202 to provide or upload the following data from the fuel outlet of the fifth fuel transfer location 110E: the location ID information; digital tag information; transferred fuel quantity, a time stamp for the fuel transfer operation; GPS information and location information. The seventh SSM 210G as well as the sixth SSM 210F may communicate with the client sensor module (CSM) 220 during refueling and receive information such as VIN and/or LP numbers of the vehicle, mileage on the vehicle, fuel type, GPS data, etc. The seventh SSM 210G as well as the sixth SSM 210F on fuel pumps can also control fuel nozzle electronics and activates the appropriate fuel nozzle on the fuel pump, depending on vehicle fuel type, i.e., diesel or gasoline, etc.

The CSM 220 may be located adjacent a fuel inlet of the fuel consumer location 120, i.e., a fuel tank of the vehicle driven by the vehicle's engine 130. The CSM 220 may carry a location identification (ID) information identifying the fuel consumer location 120 or the vehicle including the fuel consumer location 120. The CSM 220 may communicate with an ECU unit 230 or BCU unit of the vehicle through wired or wireless manner. The CSM 220 may receive data including mileage information (odometer information), vehicle's identification number (VIN), fuel level (FL) and fuel type (FT) information from the ECU unit 230 and stores this information in its data storage (see FIG. 6B). At fuel stations during refueling events, the CSM 220 may communicate with the SSM 110E or the SSM 110D, or both sensor modules, to exchange information. As previously mentioned, the CSM 220 on the vehicles may detect an impermissible refueling activity. If the vehicle refuels at an unknown location and the vehicle CSM may register this information in the data storage and transmit the information to the system server 202 via the SSM 110D and the SSM 110E during a subsequent refueling activity at a known fuel station that is a part of the monitored distribution network. Optionally, the CSM 220 may include a probe/sensor unit 222 in the fourth tagged fuel flow 105D flowing into the fuel consumer location 120 to read the digital tag in real time and in-situ within the digitally tagged fuel.

Figure 3A:
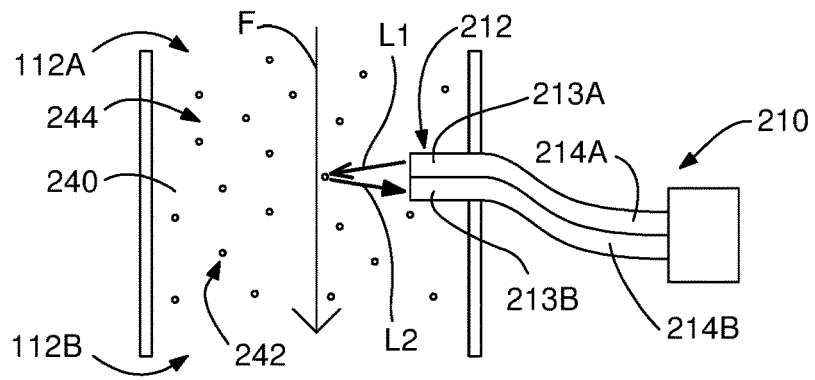
FIG. 3A is a schematic illustration of a service sensor module of the present invention, wherein the service sensor module has been shown real time reading a digital tag in the fuel.

FIG. 3A illustrates an SSM 210 reading a digital tag comprising a digital tag material 242 dispersed within a fuel matrix 244 of the digitally tagged fuel 240. As mentioned above, digital tags include information about the fuel to be monitored within the distribution network. The digital tag may be formed by the digital tag material 242 which may be comprised of one or more type of fluorescent materials. The SSM 210 may be a fiber optic sensor module including the probe 212 which is preferably extended into the digitally tagged fuel 240 flowing through exemplary fuel inlet 112A and fuel outlet 112B in the flow direction denoted with arrow 'F'.

The probe 212 may be in direct physical contact with the digitally tagged fuel or immersed into the digitally tagged fuel. As the digitally tagged fuel 240 flows through the fuel inlet 112A or the fuel outlet 112B of a fuel transfer location, the probe 212 detects the digital tag in real time. The probe 212 includes a radiation emitter portion 213A which emits a light beam L1 having a predetermined wavelength range to cause the digital tag material 242 to fluoresce with a predetermined wavelength or a signature wavelength (see also FIG. 3B). Fluorescence radiation L2 or emission emitted by the digital tag material 242, which is detected by the detector portion 213B of the probe 212, may include the specific digital tag information about the digitally tagged fuel 240. The fluorescence radiation L2 detected by the detector portion 213B of the probe is transmitted to the SSM 210 as an optical signal carrying the digital tag ID and/or digital tag information. The probe 212 may be connected to the SSM 210 using optical fibers, or the probe 212 and hence the radiation emitter portion 213A and the detector portion 213B may be the distal ends of optical fibers 214A and 214B. Optical signal received from the probe 212 through the optical fibers may be first transformed into an electrical signal and then into a digital signal at the SSM 210 and the digital signal including the information carried by the digital tag may be transmitted to the system server from the SSM 210.

In one embodiment, in the context of this application, the terms real time, online, or in-situ which may be used to describe the implementation of how the digital tag is read using the present invention generally refer to a tracking and identification operation of a digitally tagged fuel. In this respect, the tracking and identification operation may preferably be performed at a point of transfer and within the dynamic environment of flowing fuel or being transferred fuel so that any quality indicators or any information identifying the fuel carried by the digital tag may be read or detected and identified as the fuel is dynamically flowed from one fuel storage location or fuel tank to another fuel storage location or another fuel tank, or a fuel user's vehicle. As opposed to the present invention's real time reading feature, conventional techniques involve collecting test samples for testing and taking them to laborites located away from the storage areas or rely on on-field or off-field bulky analysis equipment such as spectrometers to test the fuel or liquids, often quantitatively. Many of such analysis equipment also employ separate sampling chambers on them, which can be filled with fuel or liquid samples to conduct tests using the analysis equipment.

In one embodiment, digital tag material 242 forming the digital tag may include fluorescent materials including quantum dot materials. Quantum dots are nanometer (nm) size crystal nanoparticles and their bandgap may be tuned with their particle size. Quantum dots may comprise group II-VI materials, group III-V materials, group IV-VI, and group IV materials. Quantum dots may emit radiation in the form of one of DUV, UV, VIS, NIR and IR. In one embodiment, for gasoline fuel, NIR emitting quantum dots (about 700-1000 nm) may be added as a digital tag to the gasoline since the gasoline has low background fluorescence at these wavelengths. Examples of quantum dot materials may include, but not limited to, PbS, CdS and ZnS. Such quantum dot materials may have wide absorption bands; therefore, they may be excited with a wide range of light from UV light (about 400 nm) to red light (about 700 nm). The light sources used to illuminate the quantum dot materials dispersed in the fuel may include laser diodes or light emitting diodes. Since gasoline has high absorption at UV wavelengths and absorption decreases towards higher wavelengths, the light source may be in the range of about 450 nm-650 nm.

In one embodiment, digital tag may be coded information generated by a single digital tag material or a combination of digital tag materials. The coded information or digital tag ID carried by the digital tag may be configured as a barcode. In this respect the code may include a predetermined series of digits or predetermined group of numbers. Each code refers to a previously defined fuel identity indicators, which are previously stored in the system 202 such as product number, fuel type, brand name, company name, country, quality indicators, tax status etc., which are mentioned above. The coded information may be generated using a combination of fluorescent particles having different wavelengths and concentrations. Each digital tag material forming the digital tag may have identifiable emission or radiation wavelengths and emission intensity levels.

Figure 3B:
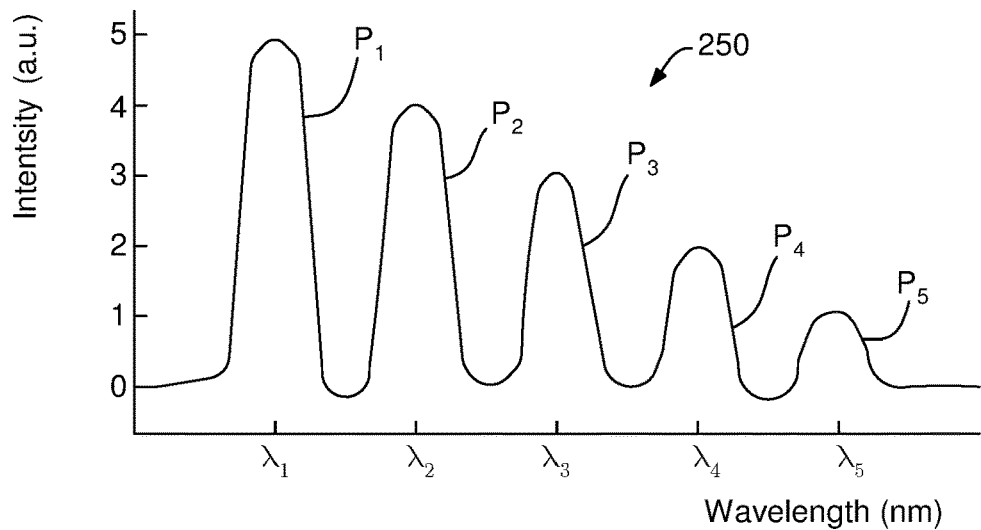
FIG. 3B is a graph showing an exemplary fluorescence emission spectrum of a digital tag.

FIG. 3B shows an exemplary fluorescence emission spectrum 250 of an exemplary digital tag having exemplary emission peaks such as the peaks $P_1$, $P_2$, $P_3$, $P_4$ and $P_5$. The fluorescence emission spectrum 250 may be the same as the fluorescence radiation L2 detected by the fiber optic sensor module, SSM 210 shown in FIG. 3A. The emission peaks $P_1$-$P_5$ may form distinctively when the digital tag is excited or illuminated with a light source as described above. In the exemplary emission spectrum 250, the emission peak $P_1$ may form at a wavelength $\lambda_1$ with an intensity $I_5$, $P_2$ may form at a wavelength $\lambda_2$ with an intensity $I_4$, $P_3$ may form at a wavelength $\lambda_3$ with an intensity $I_3$, $P_4$ may form at a wavelength $\lambda_4$ with an intensity $I_2$, and $P_5$ may form at a wavelength $\lambda_5$ with an intensity $I_1$. The emission peak $P_1$ may have the shortest wavelength $\lambda_1$ and the highest arbitrary intensity value $I_5$, and the emission peak $P_5$ may have the longest wavelength in this digital tag. In this respect, for the emission peaks $P_1$-$P_5$ corresponding wavelengths and arbitrary intensity values may be ordered as $\lambda_1<\lambda_2<\lambda_3<\lambda_4<\lambda_5$ and $I_1<I_2<I_3<I_4<I_5$ respectively.

As an example, $\lambda_1$ may be about 500 nm, $\lambda_2$ may be about 600 nm, $\lambda_3$ may be about 700 nm, $\lambda_4$ may be about 800 nm and $\lambda_5$ may be about 900 nm for the digital tag having the emission spectrum 250. Exemplary concentration levels of the fluorescent nanoparticles for the same example may be 500 ppb for $P_1$, 400 ppb for $P_2$, 300 ppb for $P_3$, 200 ppb for $P_2$ and 100 ppb for $P_1$. It is understood that the emission spectrum 250 may be formed by five different materials each having either the same particle size or each having different particle sizes or any combination of the same and different size particles for five different materials. Furthermore, five different materials may be introduced into the fuel: either with five different concentration levels, i.e., each material having its own unique concentration, or the all the materials having the same concentration level, or less than five concentration levels, i.e., at least two of the materials having the same concentration level. The emission spectrum 250 may also be formed by the same material having five different particle sizes. Five different material sizes may be introduced into the fuel: either with either each particle size having its concentration level, or all the particle sizes having the same concentration level, or less than 5 concentration levels, i.e., at least two of the particle sizes having the same concentration level. The emission spectrum 250 may also be formed with various mixtures of such material types and sizes at five of less than five concentration levels.

In this embodiment, each emission peak of the spectrum acts as a bit and emission peaks of the emission spectrum 250 all together form a code. When the emission spectrum 250 is received by an SSM 210 of the system of the present invention as an optical signal, it is transformed into a digital signal or a code having digits ordered as 54321 and this code is transmitted to system server by the SSM. As explained above this code may refer to a plurality of information about the fuel. This way, different or the same fluorescent nanomaterials with different emission peaks and different intensity may be used to create different spectrums identifying different codes for digital tags. By controlling or tuning the size, type, concentration and mixtures of the digital tag materials including the fluorescent nanomaterials, a plurality of codes as digital tags may be configured and added to the fuel, wherein each digital tag generates a different emission spectrum referring to a specific code and related or an assigned information about the fuel. For example a first emission spectrum may include a first information; a second emission spectrum includes a second information, a third emission spectrum includes a third information and so on.

Emission spectrums of the present invention may be formed in a spectrum wavelength range of about 200 nm to 2000 nm.

In one embodiment, in a first method, a digital tag may be formed using a fluorescent nanomaterial having different particle sizes, for example, using the same material in three particle sizes to generate a plurality of emission spectrums for digital tags. In this example, a first particle size may be larger than a second particle size and a third particle size, or the second particle size may be larger than the first and the third particle sizes, and so on. In this context, particle size or diameter refers to the largest distance across a particle. Since each size may have its own intensity and wavelength a plurality of specific emission spectrums may be formed by mixing the particles. In a second method, another digital tag may be formed using a mixture of different nanomaterials having the same or different particle sizes, such as a first nanomaterial, a second nanomaterial, a third nanomaterial and so on. Many specific emission spectrums for digital tags may be created using a mixture of different nanomaterials having the same or different particle sizes. In addition in a third method, digital tags may be formed by preparing the above described the first or the second method materials with the same or different sizes in various concentration levels to form the digital tags having different emission spectrums. For example, if the digital tag material includes a composition including three different fluorescent nanomaterials with different wavelengths and if each of these fluorescent materials has 10 different intensity levels at ten concentration levels, 999 barcodes can be generated from this digital tag composition. In some embodiments, fluorescent nanomaterial concentration levels may be in the range of about 1 ppb –100 ppm, or about 10 ppb-10 ppm, or about 100 ppb-1 ppm. In some embodiments, nanoparticle sizes may be in the range of about 1-100 nm, or about 1-50 nm, or about 1-40 nm, or about 1-30 nm, or about 1-20 nm, or about 1-10 nm, or about 2-10 nm.

Different from the embodiment using florescence radiation, alternatively, the sensor module may also employ a sensing mechanism based on absorbance or transmittance measurements. In this embodiment, digital tag materials having specific absorbance characteristics at specified wavelengths ranging from DUV to IR may be used. Absorption of an applied radiation by the fuel, which contains the digital tag, is proportional to the concentration of the digital tag material in the fuel. Accordingly, by measuring absorption or transmission of the applied radiation at specific wavelengths that are defined by different materials that form the digital tag, the digital tag information can be obtained.

Figure 3C:
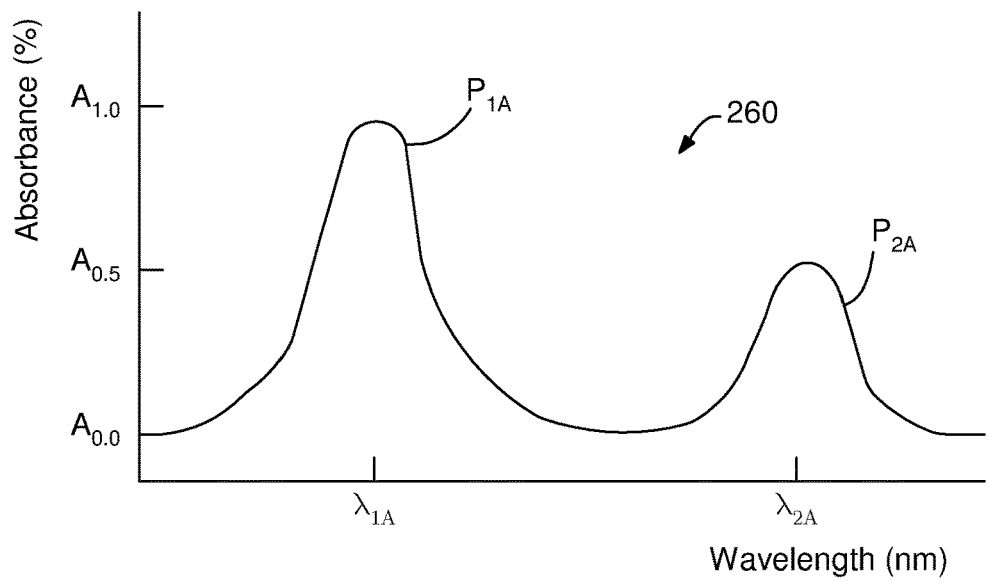
FIG. 3C is a graph showing an exemplary absorbance spectrum of a digital tag.

FIG. 3C shows an exemplary absorbance spectrum 260 of an exemplary digital tag having exemplary absorption peaks such as the peaks $P_{1A}$ and $P_{2A}$. The absorbance value $A_0$ is the absorbance value of the fuel for a specific wavelength range, which is about 0% or a value above and close to 0. The emission peaks $P_{1A}$ and $P_{2A}$ of the absorbance spectrum 260 may form distinctively when the digitally tagged fuel is excited with a broadband light source. In the exemplary absorbance spectrum 260, the absorbance peak $P_{1A}$ may form at a wavelength $\lambda_{1A}$ with an absorbance value of $A_1$ (about 100%), $P_{2A}$ may form at a wavelength $\lambda_{2A}$ with an absorbance value $A_{0.5}$ (about 50%). As an example, $\lambda_{1A}$ may be about 800 nm, $\lambda_{2A}$ may be about 900 nm for the digital tag in the fuel. In this spectral configuration each absorbance peak acts as a bit and all together form a code. The exemplary absorbance spectrum 260 may form a code having digits ordered as 21.

In one embodiment, fluorescent nanomaterials which fluorescence at specific wavelengths at predetermined concentrations may be used to form a digital tag to track the integrity of the digitally tagged fuel. In this embodiment, any change in the concentration of the fluorescent nanomaterial or digital tag material in the tracked fuel, having a known wavelength and an intensity value at this wavelength, may change the intensity value for that wavelength, i.e., changes in concentration may result in changes in the emission intensity values while the wavelength remains unchanged. This way, by tracking intensity values at specific wavelengths, changes in the digital tag concentrations may also be tracked. If a deviation or change in the intensity values is detected during any of the fuel transfers, this may indicate a concentration change for the fluorescent nanomaterial, which may be translated as some other liquid or fuel is mixed into the digitally tagged fuel. In fact, in one embodiment, this deviation in intensity may be used to determine the amount of liquid or fuel which may be illegally mixed into a digitally tagged fuel. For example, an exemplary branded or approved fuel, such as gasoline, may be digitally tagged with an exemplary fluorescent nanomaterial having a concentration of about 1 ppm by mixing it into the branded fuel to provide a predetermined emission at about 800 nm with an intensity peak of about 1000 units to track at sensor readings. Accordingly, throughout the fuel transfer operations from one location to other, service sensors modules should read 1000 units for this digitally tagged fuel at each transfer location. Any deviation from this predetermined digital tag reading may indicate a change in the concentration of the digital material or the fluorescent nanomaterial. For example, at one of the fuel transfer locations, if the intensity peak is read as about 900 units at about 800 nm, this may indicate a digital tag concentration of about 0.9 ppm which may further indicate that the digitally tagged fuel is mixed or diluted with some other liquid or fuel with a volume ratio of about 10%. In this manner a liquid or fuel mixed into a branded or approved fuel can be quantified. It will be appreciated that the emission intensity and wavelength values used in this example may be exemplary values, thus the same may be done for deviations from any intensity values within the emission spectrum wavelength range of about 200 nm to 2000 nm. In all the embodiments fuel may include gasoline and the digital tags may include PbS, CdS and ZnS quantum dot materials.

By utilizing the above described coding or barcoding scheme, the digital tag may carry data including various specifications or information about the fuel. Digital tag may be configured as one or more digital tags having codes including information about the fuel, such as an authorization code for the fuel which may provide proof for integrity of the fuel, indicating that the fuel is approved, and thus there is no tax evasion. Furthermore, the digital tag may include a fuel type code that indicates if the fuel is gasoline, diesel, etc., and a company code that identifies the distributer of the fuel, a trademark for the fuel and a region code which indicates the origin of the fuel such as in the form of region ID, terminal ID, etc. In this application, digital tag refers to either a single digital tag carrying a multiple information codes or a plurality of digital tags carrying a plurality of information codes related to the fuel that is being monitored within the fuel distribution network.

Figure 4A:
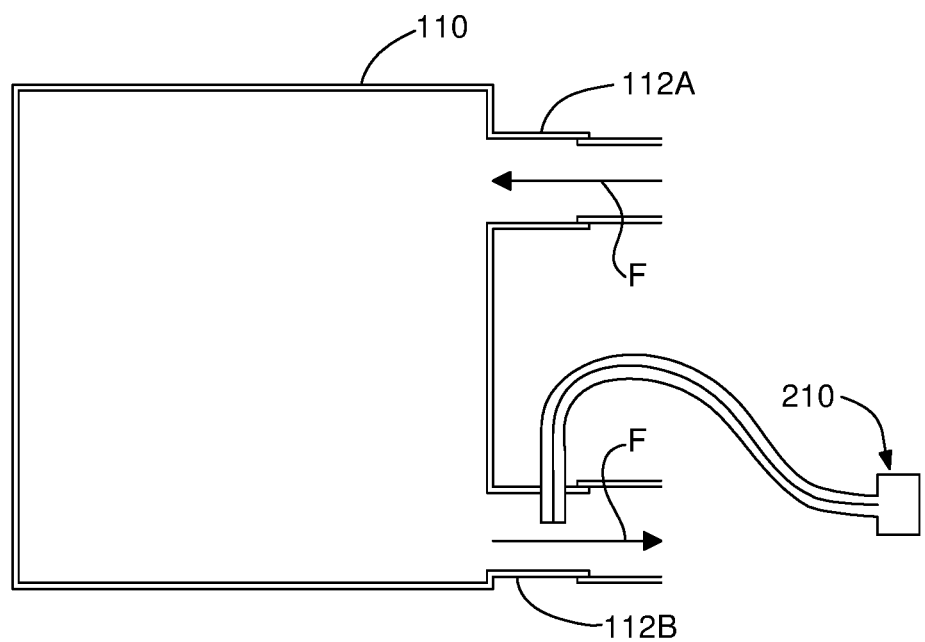
FIGS. 4A-4B are schematic illustrations showing service sensor modules disposed at fuel inlets and fuel outlets of various fuel transfer locations.
Figure 4B:
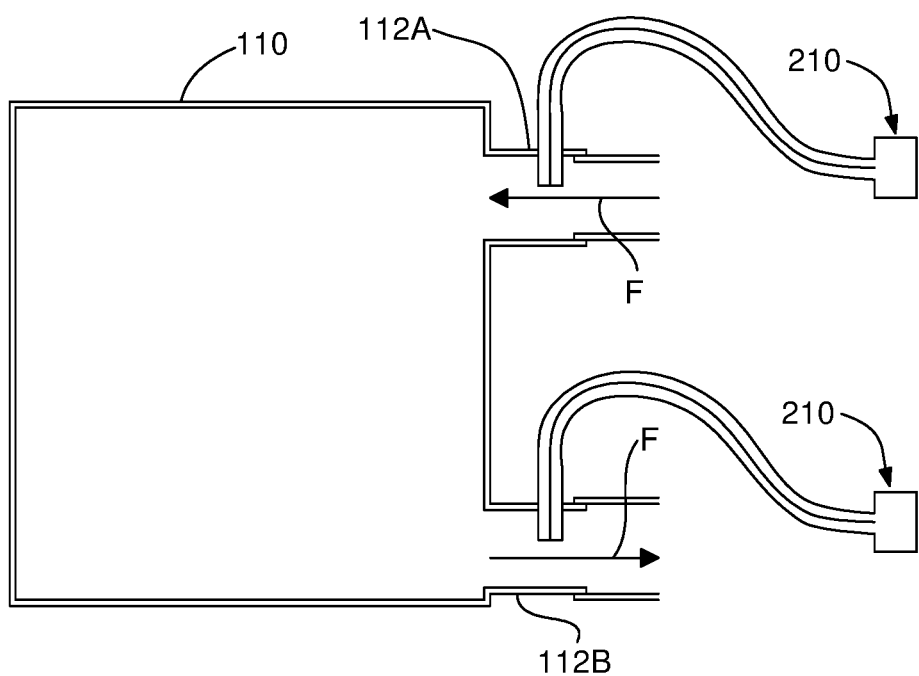

FIGS. 4A and 4B exemplify various installation configurations for the SSMs 210 on various fuel transfer locations 110. FIG. 4A shows a fuel transfer location 110 having a fuel inlet 112A and a fuel outlet 112B. A single SSM 210 may be installed at the fuel outlet 112B and real time reads digital tag information in the digitally tagged fuel as the digitally tagged fuel flows through the fuel outlet 112B in the direction of arrow 'F'. In FIG. 4A, the fuel transfer location 110 may exemplify the first fuel transfer location 110A, e.g., a fuel terminal or a refinery storage tank, having the first SSM 210A at the fuel outlet 212A (FIG. 2).

FIG. 4B shows a fuel transfer location 110 configured to have two SSM 210 installed at a fuel inlet 112A and a fuel outlet 112B of the fuel transfer location 110. In this configuration, the digitally tagged fuel is flowed into the fuel transfer location 110 through the fuel inlet 112A in the direction of arrow 'F' while the digital tag information is read in real time by the SSM 210 installed at the fuel inlet, and the digitally tagged fuel is flowed out of the fuel transfer location 110 through the fuel outlet 112B in the direction of arrow 'F' while the digital tag information is read in real time by the SSM 210 installed at the fuel outlet 112B. Referring to FIG. 4B and FIG. 2, the fuel transfer location 110 may exemplify any one of: the second fuel transfer location 110B, e.g., the fuel tanker truck, having the second SSM 210B installed at the fuel inlet and the third SSM 210C installed at the fuel outlet; or the third fuel transfer location 110C, e.g. the gas station storage tank, having the fourth SSM 210D installed at the fuel inlet and the fifth SSM 210E installed at the fuel outlet; or the combination of the fourth and fifth fuel transfer locations 110D and 110E, e.g., the gas station fuel pump and the pump gun or nozzle, having the sixth SSM 210F installed at the fuel inlet of the pump and the seventh SSM 210G installed at the fuel outlet of the pump or the nozzle.

Figure 5:
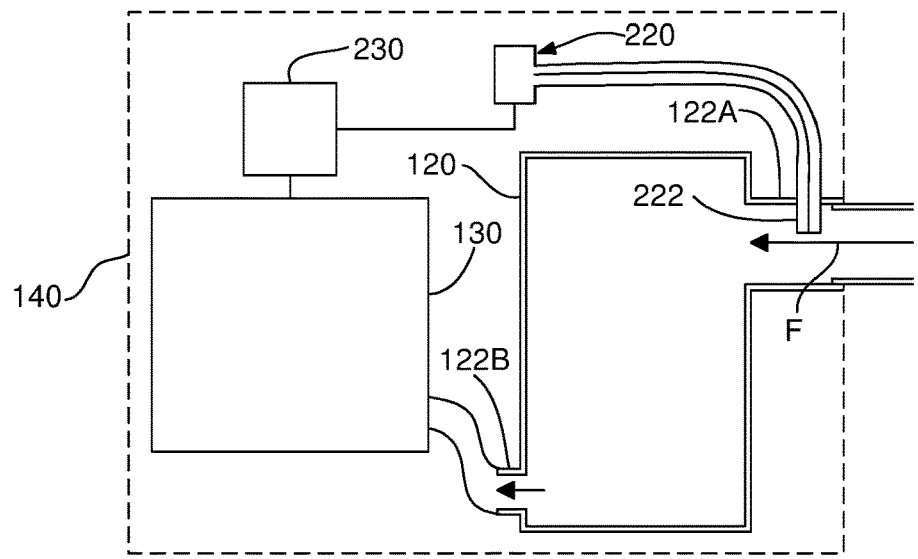
FIG. 5 is a schematic illustration showing a client sensor module disposed at a vehicle having an ECU unit.

FIG. 5 exemplifies an installation configuration for the CSM 220 on the fuel consumer location 120 of a vehicle 140, for example, the fuel tank of the vehicle 140 such as a car or truck, etc., having the vehicle engine 130. The fuel consumer location 120 having a fuel inlet 122A and a fuel outlet 122B. A single CSM 220 may be installed adjacent the fuel consumer location 120, optionally at the fuel inlet 122A. The CSM 220 may communicate with the ECU unit 230 or BCU unit through wired or wireless manner. Optionally, the probe 222 of the CSM 220 may be located at the fuel inlet 122A so as to real time read digital tag information in the digitally tagged fuel as the digitally tagged fuel flows through the fuel inlet 112A in the direction of arrow 'F'. The digitally tagged fuel is filled into the fuel consumer location 120 is consumed by the vehicle as it is operated.

Figure 6A:
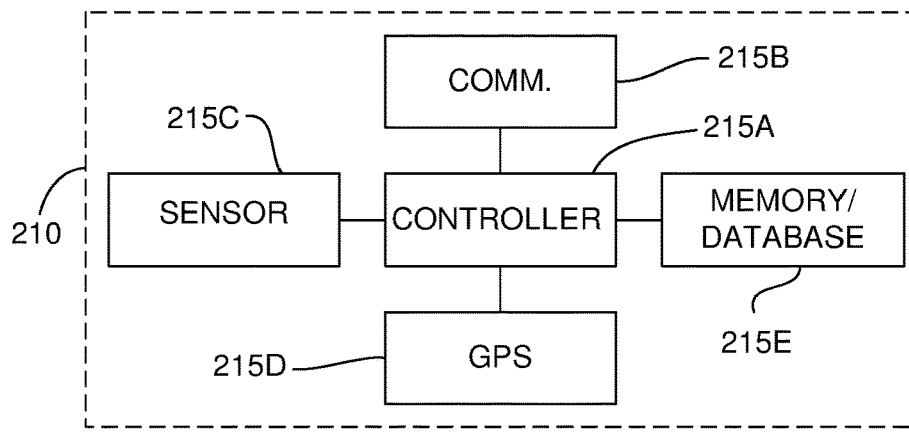
FIG. 6A is a schematic diagram of a service sensor module (SSM)

FIG. 6A shows an exemplary structure of the service sensor modules SSMs 210 used in the system 200. Accordingly the SSM 210 may comprise: a controller 215A such as a CPU; a communication unit 215B, such as a transmitter receiver (transceiver), to communicate with the system server, other SSMs and the CSMs to receive or transmit data, wirelessly or wired; a sensor unit 215C including an emitter and a detector (not shown) connected to the sensor probe via optical fibers to detect digital tag in the digitally tagged fuel; a GPS unit 215D to determine the global position of the SSM 210; a memory and data unit 215E to store all the data collected by the sensor unit 215C, the GPS unit 215D, and the data received by the communication unit 215B. The memory and data unit 215E may also include an operation software and computer instructions to operate the SSM 210. The emitter of the sensor unit 215C comprises a light source comprising a laser diode or a light emitting diode with a preferred emission wavelength that is transferred via sensor probe (FIG. 3A) to the digitally tagged fuel and used to excite the digital tag material in the fuel.

The sensor probe receives the fluorescence emission from the digital tag and transmits it as an optical signal to the detectors in the sensor unit 215C, which may be for example a silicon based photodiode and/or GaAs based photodiode with probably a band selective filter to read the specific digital tag. In the sensor unit 215C, this optical signal including the ID or code carried by the digital tag is transformed into a digital signal which is sent to the system server by the controller 215A. Employing the emitter and detectors, the sensor unit 215C reads the digital tag in real time manner. The memory and data unit 215E also stores the ID of the SSM 210, quantity of the transferred fuel, GPS location of the SSM 210, digital tag information of the transferred fuel and the timestamp of the fuel transfer operation. The data stored or kept in the memory and data unit 215E may be transmitted to the system server 202 (FIG. 2) either wirelessly or using a wired connection. The units 215B, 215C, 215D and 215E are all connected to the controller 215A. Each SSM 210 may also have a power unit (not shown) to power the SSM.

Figure 6B:
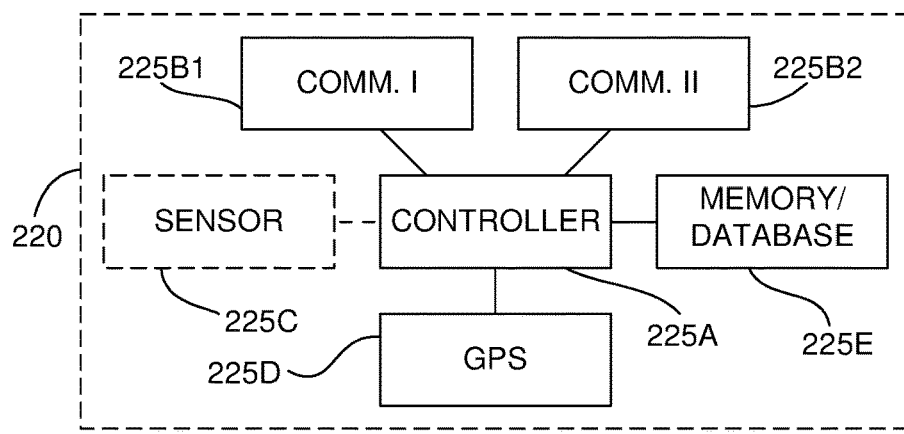
FIG. 6B is a schematic diagram of a client sensor module (CSM)

FIG. 6B shows an exemplary structure of the client sensor module 220 used in connection with system 200. Accordingly the CSM 220 may include: a controller 225A such as a CPU; a first communication unit 225B1 to communicate with the SSMs to receive or transmit data; a second communication unit 225B2 to communicate with the ECU unit 230 (electrical control unit) or BCU unit (body control unit) of the vehicle; an optional sensor unit 225C including an emitter and a detector (not shown) connected to the sensor probe via optical fibers to detect digital tag information in the digitally tagged fuel; a GPS unit 225D to determine the global position of the CSM 220; a memory and data unit 215E to store all the data collected by the GPS unit 225D as well as the first and second communication units 225B1 and 225B2. The first and second communication units 225B1, 225B2 may be transmitter receivers (transceivers) operating wirelessly or wired. The memory and data unit 225E stores the GPS location of refueling or the location of the service stations where the fuel is purchased, ID of the fuel pump at the gas station, mileage information during refueling, quantity of the fuel filled to the vehicle, digital tag information of the digitally tagged fuel, and the timestamp of the refueling operation. In particular, the sixth and seventh SSMs 210F and 210G (FIG. 2) located on the fuel pump and the fuel nozzle may receive the vehicle identification number (VIN), vehicle license plate number (LPN), fuel type of the vehicle and mileage information from the CSM 220 on the vehicle via the communication unit 215B of the SSM 210 and the during refueling of the vehicle at the gas station. The memory and data unit 225E may include an operation software and computer instructions to operate the CSM 220. The CSM 220 may include other smart units or modules such as a fuel level sensor module.

As described above the system 200 enables a platform that the digitally tagged fuel can be tracked, for example, starting from a refinery to the user vehicles by means of digital tag to check if the fuel is approved in terms of quality and quantity. The system 200 also enables organizations to trackback the history of the fuel with help of the information from all the tracking points including the fuel transfer locations and the consumer fuel locations, i.e., tracking the fuel filled into the gas tank of a vehicle in terms of the service station that the vehicle is refueled, the tanker that brings fuel to that gas station, the refinery or terminal that the tanker takes the fuel initially from. The system 200 also enables organizations to track the quantity of the fuel that is circulating through a fuel distribution network and make sure that no fuel is lost during the distribution. The system 200 may also enable organizations to track the GPS position of the fuel transfers at transfer locations and refueling of vehicles at the service stations. The system 200 also enables organizations to track vehicles by their VIN and/or license plate and store the refueling information by their mileage and refueled quantity. This large amount of information registered on the system 200 may be advantageously utilized for development of many business models.

Figure 7:
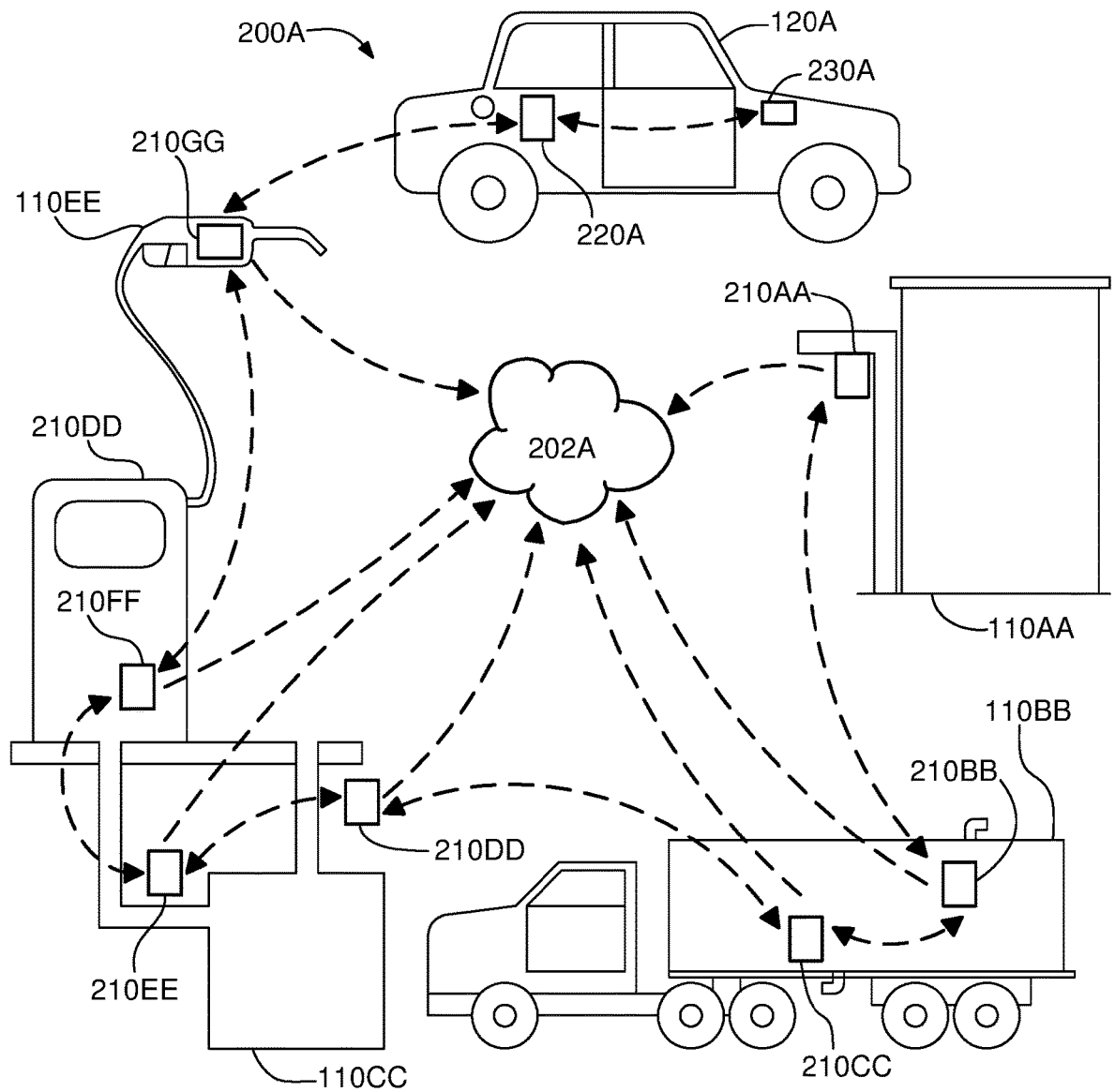
FIG. 7 is a schematic illustration of an embodiment of a gasoline tracking an identification system.

FIG. 7 shows an application example for a digitally tagged fuel transport operation monitored by an exemplary fuel tracking and identification system 200A. Digitally tagged gasoline is first loaded to a tanker truck 110BB from the refinery storage tank 110AA. The tanker truck 110BB transports the digitally tagged gasoline to a gas station, and unloads the digitally tagged gasoline into a storage tank 110CC or gasoline reservoir of the gas station. When a gasoline pump 110DD of the gas station is activated to refuel a vehicle 120A such as a car, the digitally tagged gasoline is withdrawn from the storage tank 110CC by the pump 110DD and delivered to the vehicle via a gasoline nozzle 110EE. During this transport operation a first SSM 210AA of the refinery storage tank, a second SSM 210BB and a third SSM 210CC on the tanker truck, a fourth SSM 210DD and a fifth SSM 210EE of the gas station storage tank, a sixth SSM 210FF and a seventh SSM 210GG of the fuel pump, and a CSM 220A of the vehicle, which is in connection with a ECU 230A, are all in data communication with one another and a system server 202A as depicted with dotted line arrows and as described above with respect to FIG. 2.

Figure 8:
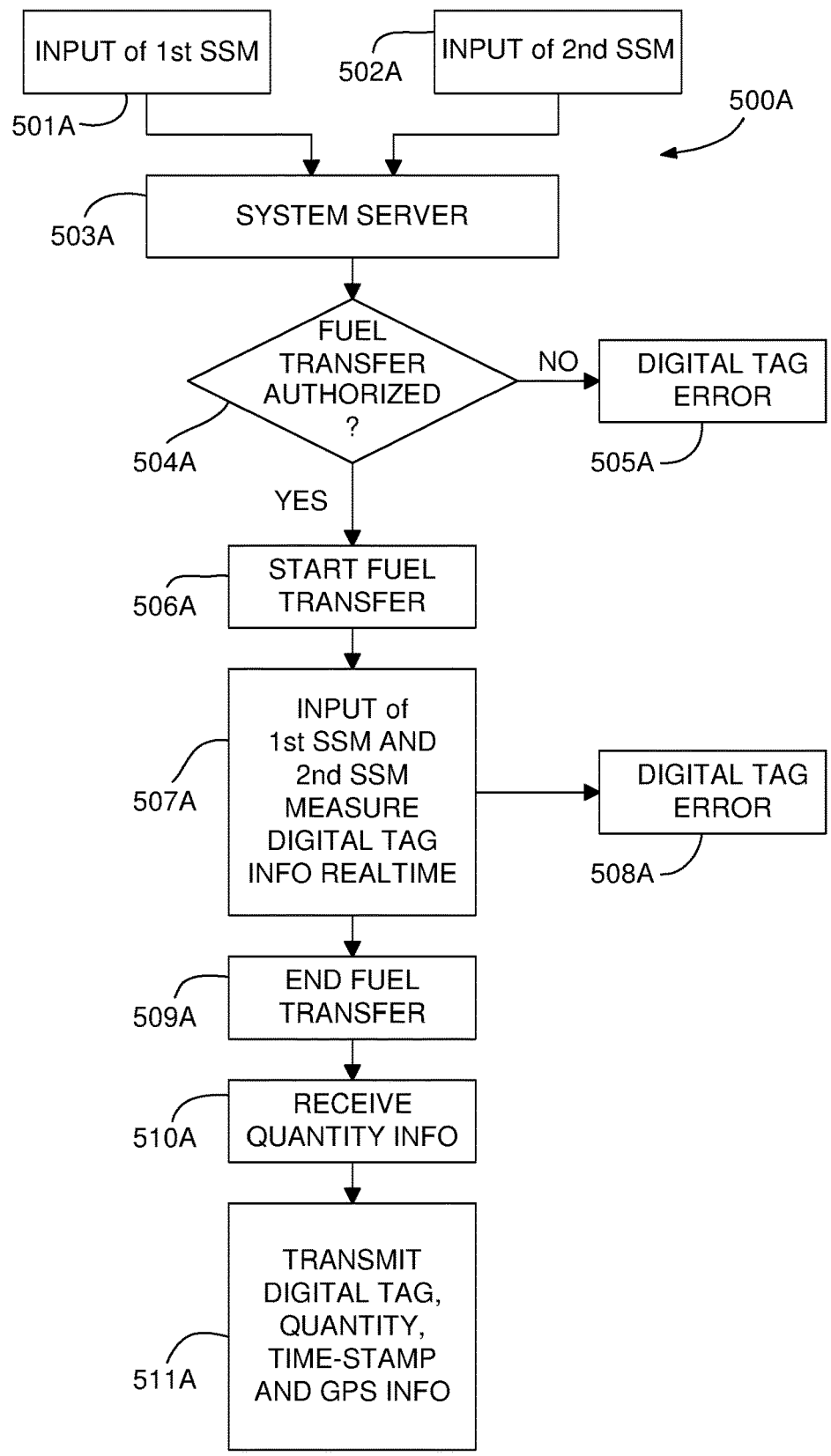
FIG. 8 is a flow chart illustrating an embodiment of an exemplary method of tracking fuel delivery from a refinery fuel storage tank to a fuel tanker truck.
Figure 9:
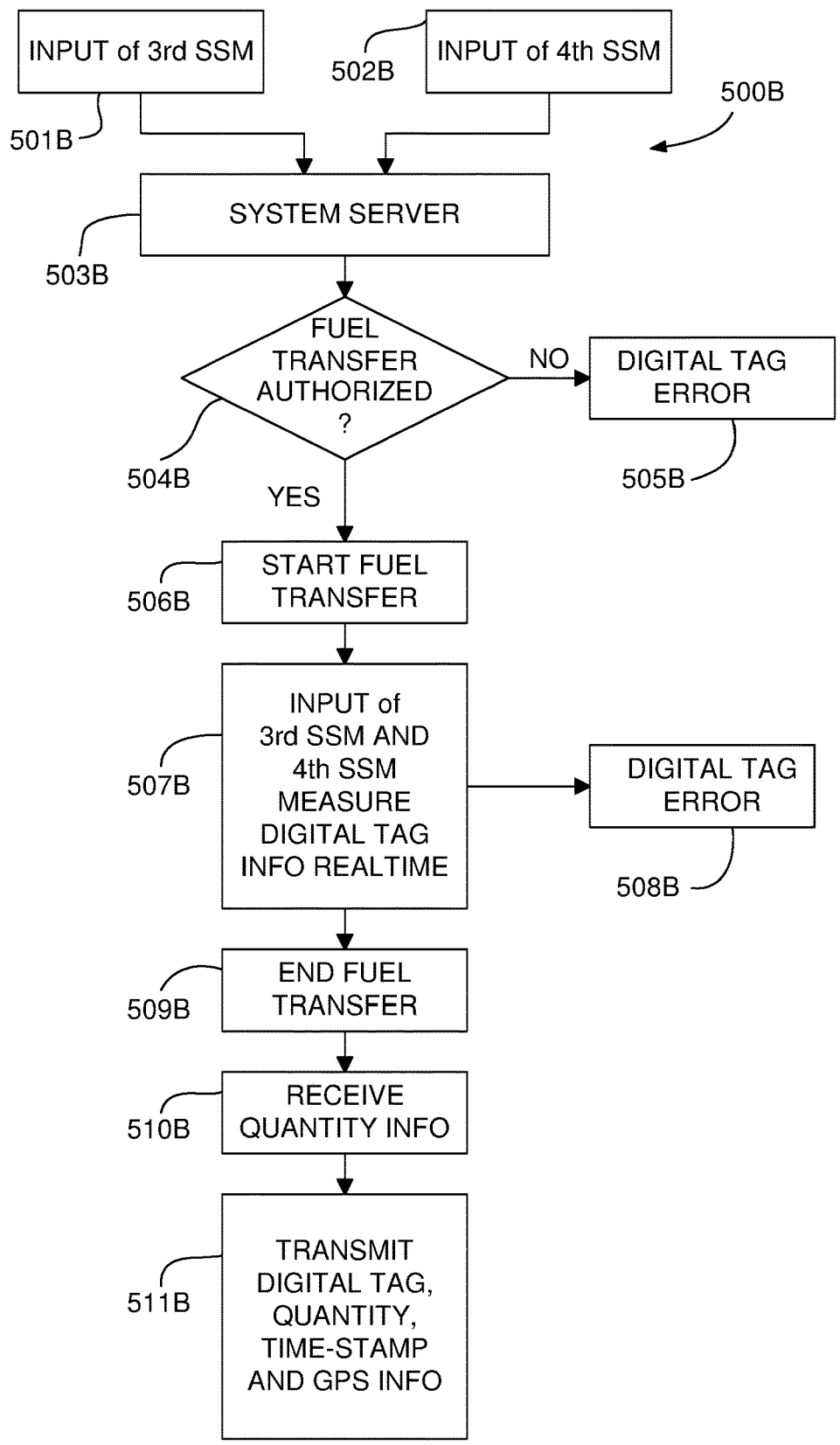
FIG. 9 is a flow chart illustrating an embodiment of an exemplary method of tracking fuel delivery from the fuel tanker truck to a fuel station storage tank.
Figure 10:
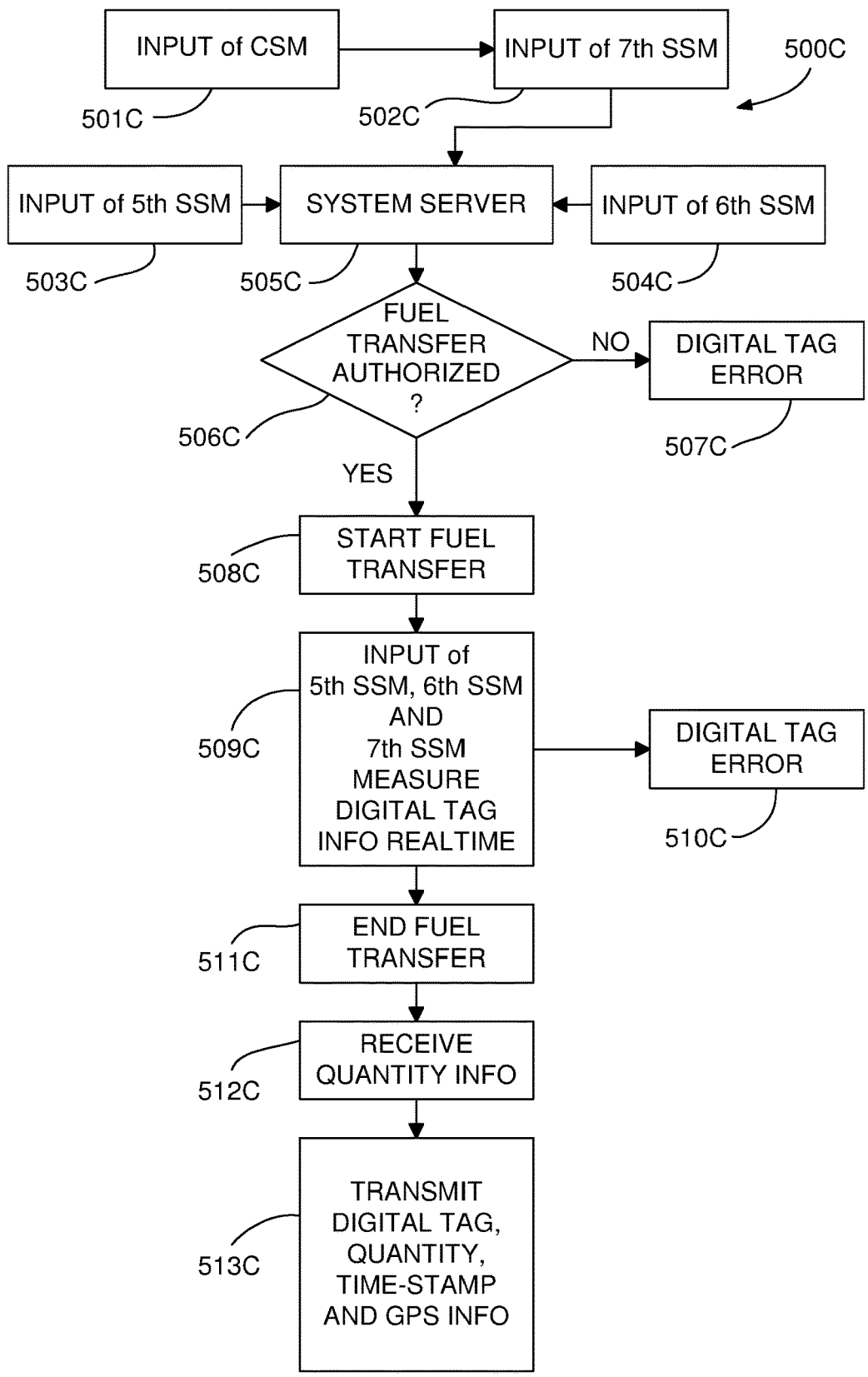
FIG. 10 is a flow chart illustrating an embodiment of an exemplary method of tracking fuel delivery from a fuel station storage tank to a vehicle fuel tank.

FIGS. 8-10 show flow charts 500A, 500B and 500C describing an exemplary embodiment of a fuel tracking and identification process of the present invention using the system 200 shown in FIG. 2.

FIG. 8 is a flow chart showing an exemplary method 500A of tracking the first tagged fuel flow 105A from the first fuel transfer location 110A (fuel terminal or fuel terminal tank) to the second fuel transfer location 110B (fuel tanker truck), which components have been shown in FIG. 2. As described above, the first SSM 210A may be at the fuel outlet of the fuel terminal tank and the second SSM 210B may be at the fuel inlet of the fuel tanker truck used to transport the digitally tagged fuel. The method 500A begins with operation steps 501A and 502A during which the first SSM 210A and the second SSM 210B start data communication process or handshake. At operation step 503A, the system server 202 receives both the fuel terminal tank ID and the fuel tanker truck ID from the first SSM 210A and the second SSM 210B respectively. Further, in operation step 501A, a quality certificate of the digitally tagged fuel in the form of the digital tag may be read or identified by the first SSM 210A and registered with the system database 204 through the system server. The quality certificate may include all the information obtained by the first SSM 210A which described above with respect to FIG. 2. A quality certificate may be prepared by analyzing the fuel according to the internationally accepted norms (ASTM or API, or EN norms) when it is produced at the refinery. In one embodiment, this quality information of the fuel, i.e., the digitally tagged fuel may be tracked and verified in each transfer location to enable further distribution of the digitally tagged fuel within the fuel distribution network.

Operation step 504A may be then performed by the system server 202 to determine whether the ID data about the transfer locations submitted by the first SSM 210A and the second SSM 210B is approved. If the ID data is not approved, operation step 505A is performed to generate an alert signal by the server and, optionally, to block any fuel transfer from the fuel terminal tank to the fuel tanker truck. If the ID data is approved, operation step 506A is performed by starting and allowing the tagged fuel flow from the fuel terminal tank to the fuel tanker truck. As soon as operation step 506A begins, operation step 507A is performed to recheck the integrity of the digital tag using real time readings of the first SSM 210A and the second SSM 210B and this data is transmitted to the system server. Operation step 507A involves matching the digital tag information from the first SSM 210A and the second SSM 210B from operation step 507A with the original digital tag information that was read in operation step 501A. Alternatively, the original digital tag information may be stored in the system 200 prior to the distribution of the fuel, prior to operation step 501A. If the digital tag readings don't match in operation step 507A, an alert signal is produced by the system server in operation step 508A and, optionally, the fuel transfer may be blocked. If the digital tag readings match, the digitally tagged fuel continues to flow into the fuel tanker truck until operation step 509A. Between the operation steps 506A and 509A, the first SSM 210A and the second SSM 210B may continuously take readings of the digital tag and feed the data to the system server 202.

Once the digitally tagged fuel transfer is completed, operation step 510A is performed to receive the transferred fuel quantity data involving the amount of the digitally tagged fuel, which is sent to the tanker truck, from the gauges of the fuel tanker truck and from a gauge on a pump of the fuel loading station associated with the fuel terminal tank or fuel terminal location. The fuel quantity data is received by the first SSM 210A and the second SSM 210B. Operation step 511A is then performed to transmit the digital tag information, fuel quantity information, time stamp information and the GPS information to the system server.

Specifically, the first SSM 210A may transmit the following information in encrypted form to the system server: (a) I.D. of the fuel terminal tank; (b) quantity of the transferred digitally tagged fuel; (c) GPS location of the fuel terminal tank; (d) digital tag information of the transferred digitally tagged fuel; and, (e) time stamp of the transfer operation including transfer date and time information. The second SSM 210B may transmit the following information in encrypted form to the system server: (a) I.D. of the fuel tanker; (b) quantity of the digitally tagged fuel loaded to the fuel tanker; (c) GPS location of the fuel tanker; (d) digital tag information of the loaded fuel; (e) and, time stamp of the fuel loading operation including loading date and time. After receiving and storing the encrypted information sets from the first SSM 210A and the second SSM 210B, these two information sets may be compared at the system server 202 and the transaction is approved.

FIG. 9 is a flow chart showing an exemplary method 500B of tracking the second tagged fuel flow 105B from the second fuel transfer location 110B (fuel tanker truck) to the third fuel transfer location 110C (fuel station storage tank), which components have been shown in FIG. 2. As described above, the third SSM 210C may be at the fuel outlet of the fuel tanker truck transporting the digitally tagged fuel from the fuel terminal to the fuel station and the fourth SSM 210D may be at the fuel inlet of the fuel station storage tank. The method 500B begins with operation steps 501B and 502B during which the third SSM 210C and the fourth SSM 210D start data communication process or handshake. At operation step 503B, the system server 202 receives both the fuel tanker truck ID and the fuel station storage tank ID from the third SSM 210C and the fourth SSM 210D respectively.

Operation step 504B may be then performed by the system server 202 to determine whether the ID data about the transfer locations submitted by the third SSM 210C and the fourth SSM 210B is approved. If the ID data is not approved, operation step 505B is performed to generate an alert signal by the server and, optionally, to block any fuel transfer from the fuel tanker truck to the fuel station storage tank. If the ID data is approved, operation step 506B is performed by starting and allowing the tagged fuel flow from the fuel tanker truck to the fuel station storage tank. As soon as operation step 506B begins, operation step 507B is performed to recheck the integrity of the digital tag using real time readings of the third SSM 210C and the fourth SSM 210D and this data is transmitted to the system server. Operation step 507B involves matching the digital tag information from the third SSM 210C and the fourth SSM 210D that is read in operation step 507B with the digital tag information of the digitally tagged fuel which was registered with the system server when the fuel tanker truck was loaded, and which identifies the digitally tagged fuel in the fuel tanker truck. If the digital tag readings don't match in operation step 507B, an alert signal is produced by the system server in operation step 508B and, optionally, the fuel transfer may be blocked. If the digital tag readings match, signifying no adulteration suspected, the digitally tagged fuel continues to flow into the fuel tanker truck until operation step 509B. Between the operation steps 506B and 509B, the third SSM 210C and the fourth SSM 210D may continuously take readings of the digital tag and feed the data to the system server 202.

Once the digitally tagged fuel transfer is completed, operation step 510B is performed to receive the transferred fuel quantity data involving the amount of the digitally tagged fuel, which is sent to the system server, from the gauges of the fuel tanker truck and from a fuel gauge associated with the fuel station storage tank. The fuel quantity data is received by the third SSM 210C and the fourth SSM 210D. Operation step 511B is then performed to transmit the digital tag information, fuel quantity information, time stamp information and the GPS information to the system server 202. Specifically, the third SSM 210C may transmit the following information in encrypted form to the system server: (a) I.D. of the fuel tanker; (b) quantity of the digitally tagged fuel transferred from the fuel tanker; (c) GPS location of the fuel tanker; (d) digital tag information of the unloaded fuel; (e) and, time stamp of the unloading operation including unloading date and time information. The fourth SSM 210D may transmit the following information in encrypted form to the system server: (a) I.D. of the fuel station storage tank; (b) quantity of the digitally tagged fuel loaded; (c) GPS location of the fuel station storage tank; (d) digital tag information of the loaded digitally tagged fuel; and, (e) time stamp of the loading operation including loading date and time information. After receiving and storing the encrypted information sets from the third SSM 210C and the fourth SSM 210D, these two information sets may be compared at the system server and if they match the transaction is approved.

FIG. 10 is a flow chart showing an exemplary method 500C of tracking the transfer of fuel to the fuel consumer location 120, i.e., the vehicle such as a car, from the third fuel transfer location 110C, i.e., the fuel station storage tank via the combination of the fourth fuel transfer location 110D, i.e., the fuel pump, and the fifth fuel transfer location 110E, i.e., the pump nozzle or fuel dispenser device. As described above, the third tagged fuel flow 105C delivers the digitally tagged fuel from the fuel outlet of the fuel station storage tank to the inlet of the fuel pump and the fourth tagged fuel flow 105D is delivered from a fuel outlet of the nozzle of the fuel pump to the vehicle, which components have been shown in FIG. 2. As described above, the fifth SSM 210E may be at the fuel outlet of the fuel station storage tank holding the digitally tagged fuel, the sixth SSM 210F may be at the fuel inlet of the fuel pump, the seventh SSM 210G may be at the fuel outlet of the nozzle and the CSM 220 is on the vehicle.

The method 500C begins with operation steps 501C and 502C during which the CSM 220 and the seventh SSM 210G start data communication process or handshake, preferably when the vehicle arrives at the fuel station for refueling. The CSM 220 stores the vehicles identification number (VIN), fuel type (FT) information on its memory and updates the fuel level (FL) and vehicle mileage information en route. The seventh SSM 210G receives vehicle GPS information from the CSM 220 and compares this information with the GPS information from the seventh SSM 210G. Then the seventh SSM 210G registers both GPS information and the fuel station pump ID, which is available on the seventh SSM 210G, to the memory unit of the CSM 220 with a timestamp. This information stored in the CSM 220 is used to track the vehicle refueling locations. Next, the seventh SSM 210G collects the vehicle identification data such as VIN number and license plate number either from the CSM 220 or manually from an operator working for the fuel station. For example, while the seventh SSM 210G may receive the vehicle identification number (VIN number) from the CSM 220, the license plate number of the vehicle may be manually entered to the SSM 210G using an input device such as a computer or a hand held license plate reader used by the operator at the service station. The seventh SSM 210G registers the vehicle identification data with the system server 202 which in turn access for example DMV (department of motor vehicles) database to verify the identity information by comparing the information from the vehicle and the information from the DMV database. The vehicle identification data from both the vehicle and the DMV database is registered to the system database 204 and the memory unit of the seventh SSM 210G. The seventh SSM 210G also receives the updated mileage information from the CSM 220 before refueling or during refueling and registers this information to the system database 204 and the memory units of the seventh SSM 210G and the CSM 220. Also before the refueling starts, the seventh SSM 210G receives the fuel type information of the vehicle from the CSM 220 and sends this information to the system server 202. The seventh SSM 210G activates the correct fuel nozzle depending on the fuel type information from the CSM 220 to start refueling process.

The method 500C follows with operation steps 503C and 504C during which the fifth SSM 210E and the sixth SSM 210F start data communication process with one another and also with the seventh SSM 210G and the CSM 220. In operation step 505C, the system server 202 receives the fuel station storage tank ID from the fifth SSM 210E and the fuel pump ID from the sixth SSM 210F and the seventh SSM 210G. Operation step 506C may be then performed by the system server 202 to determine whether the ID data about the transfer locations submitted by the fifth SSM 210E, the sixth SSM 210F and the seventh SSM 210G is approved. If the ID data is not approved, operation step 507C is performed to generate an alert signal by the server and, optionally, to block any fuel transfer from the fuel pump to the vehicle. If the ID data is approved, operation step 508C is performed by starting and allowing the digitally tagged fuel flow from the fuel pump to vehicle for refueling the vehicle. As soon as operation step 508C begins, operation step 509C is performed to recheck the integrity of the digital tag using real time readings of the fifth SSM 210E, the sixth SSM 210F and the seventh SSM 210G and this data is transmitted to the system server 202. Operation step 509C involves matching the digital tag information from the fifth SSM 210E, the sixth SSM 210F and the seventh SSM 210G that is read in operation step 509C with the digital tag information of the digitally tagged fuel which was registered with the system server 202 when the fuel station storage tank was loaded, and which identifies the digitally tagged fuel in the fuel station storage tank. If the digital tag readings don't match in operation step 509C, an alert signal is produced by the system server in operation step 510C and, optionally, the fuel transfer to the vehicle may be blocked. If the digital tag readings match, signifying no adulteration suspected, the digitally tagged fuel continues to flow into the vehicle's fuel tank until operation step 511C. Between the operation steps 508C and 511C, the fifth SSM 210E, the sixth SSM 210F and the seventh SSM 210G may continuously take readings of the digital tag in real time and feed this data to the system server 202.

Once the pumping of the digitally tagged fuel into the vehicle's fuel tank is completed, operation step 512C is performed to receive the transferred fuel quantity data involving the amount of the digitally tagged fuel, which is transferred to the system server, from the gauges of the fuel pump and from a fuel gauge associated with the fuel station storage tank. The fuel quantity data is received by the fifth SSM 210E, the sixth SSM 210F and the seventh SSM 210G. Operation step 513C is then performed to transmit the digital tag information, fuel quantity information, time stamp information and the GPS information to the system server 202.

Specifically, the fifth SSM 210E may transmit the following information in encrypted form to the system server: (a) I.D. of the fuel station storage tank; (b) quantity of the digitally tagged fuel transferred to the fuel pump; (c) GPS location of the fuel station storage tank; (d) digital tag information of the loaded digitally tagged fuel; and, (e) time stamp of the fuel transfer operation including the transfer date and time information. The seventh SSM 210G and/or the sixth SSM 210F may transmit the following information in encrypted form to the system server and the CSM 220 of the vehicle: (a) I.D. of the fuel station pump and vehicle that is being refueled; (b) quantity of the digitally tagged fuel transferred to the vehicle; (c) GPS location of the fuel station pump; (d) digital tag information of the digitally tagged fuel transferred to the vehicle; (e) timestamp information about the transfer; (f) registered data on the fifth SSM 210E, the sixth SSM 210F and the seventh SSM 210G; (g) data stored on the CMS 220.

The data stored on the CMS 220 may include the location of the refueling event, ID of the fuel pump at the fuel station, vehicle mileage information during refueling, quantity of the fuel filled to the vehicle and digital tag information. Data on the fifth SSM 210E, the sixth SSM 210F and the seventh SSM 210G may include I.D. of each SSM, quantity of the fuel transferred to the vehicle, GPS location data, digital tag information of the transferred digitally tagged fuel and the timestamp information. The sixth SSM 210F and/or the seventh SSM 210G located on the fuel pump may also include vehicle identification number (VIN), vehicle plate number (PN), fuel type of the vehicle and vehicle mileage information during refueling. The system database 204 may receive the digital tag information throughout the SSMs placed at fuel transfer locations all over the fuel distribution chain. The system database also stores vehicle ID information, GPS location information, timestamp information, transferred fuel quantity information from these fuel transfer locations. In addition, the data registered on the SSMs and CSM is also transferred to system server 202 and stored in the system database 204. After receiving and storing the encrypted information sets from the fifth SSM 210E, the sixth SSM 210F and the seventh SSM 210G, these information sets are compared at the system server 202 and if they match the transaction is approved.

The data that is formed on the system server of the system of the present invention may be further tailored and put into valuable form for government and/or companies to use. Mainly, digital tagging data collected from the fuel transfer points and fuel stations may be tailored for real time monitoring and tracking of the approved (digitally tagged) fuel throughout the distribution network. Accordingly, governments and oil companies may use this data to monitor the fuel distribution and prevent fuel adulteration or other illegal activity involving such as fuel tax evasions.

In one embodiment, international transportation companies may track the fuel loading/unloading positions of their vehicles and also may track if the fuel transported is approved with digital tag or not. Also using the present invention the data on the CSM may be tailored to extract the more realistic consumption information about the vehicles. Especially, fleet rental companies may advantageously use of the system with the same principle.

Moreover, present invention may ease the process for oil companies to apply business models such as fuel assurance systems. By tailoring the data on the SSMs and the system database, a company may track whether the vehicle is refueling from their fuel stations only and loyal to their brand or not. In addition, the companies may track their customers' behavior of fuel consumption and also measure the effectiveness of their campaigns for attracting new users to use their fuel stations.

Although aspects and advantages of the present invention are described herein with respect to certain preferred embodiments, modifications of the preferred embodiments will be apparent to those skilled in the art. Thus the scope of the present invention should not be limited to the foregoing discussion, but should be defined by the appended claims.

We claim:

1. A method of real time tracking transportation of a fuel, which is liquid, in a fuel distribution network, comprising:
providing a system server of the fuel distribution network configured to be in communication with a plurality of sensor modules disposed in a plurality of locations throughout the fuel distribution network, the system server including a system database, wherein the sensor modules are configured to measure fluorescence radiation from nanoparticles mixed with the fuel and to generate fuel digital identifications based on the intensity levels of the peaks measured in the fluorescence radiation;
forming nanoparticles emitting a specific fluorescence radiation when excited in the fuel;
mixing the nanoparticles with the fuel at a fuel storage location to form a fuel-nanoparticle mixture which is liquid;
measuring the specific fluorescence radiation from the fuel-nanoparticle mixture using a sensor module of the fuel storage location;
using the sensor module, generating a fuel digital identification based on the intensity peaks of the specific fluorescence radiation to identify and record the fuel-nanoparticle mixture at the fuel storage location;
using the sensor module, transmitting the fuel digital identification of the fuel-nanoparticle mixture at the fuel storage location to the system server and storing in the system database;
flowing the fuel-nanoparticle mixture into a gas station fuel pump, in a gas station, having a first sensor module therein;
measuring the specific fluorescence radiation from the fuel-nanoparticle mixture flowing into gas station fuel pump using the first sensor module;
using the first sensor module, generating a first fuel digital identification based on the intensity peaks of the specific fluorescence radiation to identify and record the fuel-nanoparticle mixture at the gas station fuel pump;
using the first sensor module, transmitting the first fuel digital identification of the fuel-nanoparticle mixture at the gas station fuel pump to the system server and storing in the system database;
flowing via a fuel line the fuel-nanoparticle mixture from the gas station fuel pump to a gas station fuel dispenser having a second sensor module therein, the gas station fuel dispenser being configured to flow the fuel-nanoparticle mixture from the gas station fuel pump into a fuel tank of a vehicle at the gas station during refueling;
measuring the specific fluorescent radiation from the fuel-nanoparticle mixture flowing to the gas station fuel dispenser using the second sensor module;
using the second sensor module, generating a second fuel digital identification based on the intensity peaks of the specific fluorescence radiation to identify and record the fuel-nanoparticle mixture in the gas station fuel dispenser;
using the second sensor module, transmitting the second fuel digital identification of the fuel-nanoparticle mixture at the gas station fuel dispenser to the system server and storing in the system database;
determining in the system server whether the fuel digital identification, the first fuel digital identification and the second fuel digital identification are the same to authenticate the fuel-nanoparticle mixture;
blocking refueling if the fuel digital identification, the first fuel digital identification, and the second fuel digital identification are not the same;
allowing refueling if the fuel digital identification, the first fuel digital identification, and the second fuel digital identification are the same;
generating a fuel tracking data in the system server; and
storing the fuel tracking data in the system database.

2. The method of claim 1 further comprising, prior to the step of flowing the fuel-nanoparticle mixture into the gas station fuel pump,
filling the fuel-nanoparticle mixture into a gas station storage tank having a third sensor module therein, a fuel line connecting the gas station storage tank to the gas station fuel pump;
measuring the specific fluorescence radiation from the fuel-nanoparticle mixture filled into gas station fuel tank using the third sensor module;
using the third sensor module, generating a third fuel digital identification based on the intensity peaks of the specific fluorescence radiation to identify and record the fuel-nanoparticle mixture at the gas station fuel tank; and
transmitting the third fuel digital identification identifying the fuel-nanoparticle mixture at the gas station fuel tank to the system server and storing in the system database.

3. The method of claim 1 further comprising, prior to the step of generating the tracking data, transmitting the fuel digital identification from the second sensor module to a client sensor module on the vehicle and storing it therein.

4. The method of claim 3, further comprising
using the second sensor module, receiving vehicle information stored in the client sensor module prior to the fuel-nanoparticle mixture being delivered to the fuel tank of the vehicle; and
transmitting the vehicle information to the system server and storing in the system database.

5. The method of claim 4, wherein the vehicle information including vehicle license plate number and the vehicle identification number.

6. The method of claim 4, wherein prior to the delivery of the fuel-nanoparticle mixture from the gas station fuel dispenser to the vehicle, using the system server to check the validity of the vehicle information by comparing the vehicle information to a previously registered vehicle information stored in the system database, wherein if the vehicle information is different from the previously registered vehicle information the system server generates an alert signal.

7. The method of claim 2 further comprising:
determining a first quantity information of the fuel-nanoparticle mixture with the first sensor module;
determining a second quantity information of the fuel-nanoparticle mixture with the second sensor module;
determining a third quantity information of the fuel-nanoparticle mixture with the third sensor module;
transmitting the first quantity information, the second quantity information and the third quantity information to the system server and storing in the database; and
updating the fuel tracking data in the system server and storing it in the system database.

8. The method of claim 2 further comprising:
using the first sensor module, determining GPS location information of the first sensor module;
transmitting to the system server, the GPS location information of the first sensor module;
using the second sensor module, determining GPS location information of the second sensor module;
transmitting to the system server, the GPS location information of the second sensor module;
using the third sensor module, determining GPS location information of the third sensor module;
transmitting to the system server, the GPS location information of the third sensor module; and
updating the fuel tracking data in the system server and storing it in the system database.

9. The method of claim 1, wherein the system server includes a system communication module which is configured to communicate with the system database and a plurality of external databases.

10. The method of claim 1, wherein the wavelength range of the specific fluorescence radiation is in the range of 200 to 2000 nanometers.

11. The method of claim 1, wherein the nanoparticles are fluorescent dyes.

12. The method of claim 1, wherein the nanoparticles are quantum dots.

13. The method of claim 12, wherein the quantum dots comprise group II-VI materials, group III-V materials, group IV-VI, and group IV materials.

14. The method of claim 1, wherein the nanoparticles comprise first nanoparticles having a first concentration and second nanoparticles having a second concentration.

15. The method of claim 14, wherein the first nanoparticles and the second nanoparticles are the same material.

16. The method of claim 15, wherein the first nanoparticles comprise a first diameter, and the second nanoparticles comprise a second diameter.

17. The method of claim 16, wherein the first diameter and the second diameter are different.

18. The method of claim 14, wherein the first nanoparticles and the second nanoparticles are different materials.

19. The method of claim 1, wherein the fuel digital identification is associated with at least one of a product identification, fuel type, fuel brand name, a registered trademark and fuel company.

20. The method of claim 1, wherein each sensor module includes a fiber optic sensor including a probe connected to a light emitter unit to emit light to cause nanoparticles in the fuel-nanoparticle mixture to generate the specific fluorescence radiation and a detector unit to read the specific fluorescence radiation.

\* \* \* \* \*